(12) United States Patent
Dong et al.

(10) Patent No.: US 12,064,641 B2
(45) Date of Patent: *Aug. 20, 2024

(54) BACTERICIDAL METHODS AND COMPOSITIONS

(71) Applicant: Pulsethera, Inc., Chestnut Hill, MA (US)

(72) Inventors: Pu-Ting Dong, Boston, MA (US); Jie Hui, Boston, MA (US); Ji-Xin Cheng, Newton, MA (US); Yifan Zhu, Allston, MA (US)

(73) Assignee: Pulsethera, Inc., Chestnut Hill, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,778

(22) Filed: Apr. 20, 2023

(65) Prior Publication Data

US 2023/0256261 A1    Aug. 17, 2023

Related U.S. Application Data

(63) Continuation of application No. 17/685,897, filed on Mar. 3, 2022, now Pat. No. 11,633,622, which is a
(Continued)

(51) Int. Cl.
*A61L 2/10* (2006.01)
*A61K 33/40* (2006.01)
(Continued)

(52) U.S. Cl.
CPC ............ *A61N 5/062* (2013.01); *A61K 33/40* (2013.01); *A61L 2/10* (2013.01); *A61L 2/208* (2013.01);
(Continued)

(58) Field of Classification Search
CPC .... A61N 5/062; A61N 5/0624; A61N 5/0616; A61N 2005/0635; A61L 2/10;
(Continued)

(56) References Cited

U.S. PATENT DOCUMENTS 5,744,094 A    4/1998  Castberg et al.
6,037,598 A    3/2000  Cicha
(Continued)

FOREIGN PATENT DOCUMENTS

WO    9602623 A1    2/1996
WO    2011006263 A1    1/2011
WO    2014089552 A1    6/2014

OTHER PUBLICATIONS

"Centers for Disease Control and Prevention. Active bacterial core surveillance (ABCs) report, Emerging infections program network, methicillin resistant *Staphylococcus aureus*, 2011", (available on the world wide web at http://www.cdc.gov/abcs/reports-findings/survreports/mrsa14.html, 3 pages, last updated Nov. 19, 2012).
(Continued)

*Primary Examiner* — Sean E Conley
*Assistant Examiner* — Brendan A Hensel
(74) *Attorney, Agent, or Firm* — Myers Bigel, P.A.

(57) ABSTRACT

Methods of the present invention comprise photoinactivation of catalase in combination with low-concentration peroxide solutions and/or ROS generating agents to provide antibacterial effects.

21 Claims, 21 Drawing Sheets

Related U.S. Application Data continuation of application No. 17/387,579, filed on Jul. 28, 2021, now Pat. No. 11,298,563, which is a continuation of application No. 17/005,807, filed on Aug. 28, 2020, now Pat. No. 11,110,296, which is a continuation of application No. PCT/US2020/016125, filed on Jan. 31, 2020.

(60) Provisional application No. 62/799,328, filed on Jan. 31, 2019.

(51) Int. Cl.
  *A61L 2/20* (2006.01)
  *A61L 101/02* (2006.01)
  *A61N 5/06* (2006.01)

(52) U.S. Cl.
  CPC ......... *A61N 5/0616* (2013.01); *A61N 5/0624* (2013.01); *A61L 2101/02* (2020.08); *A61L 2202/26* (2013.01); *A61N 2005/0635* (2013.01)

(58) Field of Classification Search
  CPC .. A61L 2/208; A61L 2101/02; A61L 2202/26; A61K 33/40
  See application file for complete search history.

(56) References Cited

U.S. PATENT DOCUMENTS

| | | |
|---|---|---|
| 2005/0019421 A1 | 1/2005 | Hobbs et al. |
| 2006/0229225 A1 | 10/2006 | Martin et al. |
| 2006/0269580 A1 | 11/2006 | Cole et al. |
| 2014/0334976 A1 | 11/2014 | Kanno et al. |
| 2017/0231949 A1 | 8/2017 | Kanno et al. |
| 2018/0071417 A1 | 3/2018 | Taboada et al. |
| 2018/0339073 A1 | 11/2018 | Clynne et al. |
| 2019/0022406 A1 | 1/2019 | Hill et al. |
| 2019/0247528 A1 | 8/2019 | Rodriguez |
| 2019/0328916 A1 | 10/2019 | Koponen et al. |

OTHER PUBLICATIONS

"Extended European Search Report corresponding to European Application No. 20748542.6 dated Oct. 10, 2022".

"International Preliminary Report on Patentability corresponding to International Application No. PCT/US2020/016125 mailed Aug. 12, 2021".

"Office Action corresponding to Chinese Application No. 202080022202X dated May 7, 2022".

"Reactive oxygen species", Available on the world wide web at https://en.wikipedia.org/w/index.php?itle=Reactive_oxygen_species &oldid=879625039 {Jan. 22, 2019) 27 pages.

Abraham , et al., "GROMACS: High performance molecular simulations through multi-level parallelism from laptops to supercomputers", SoftwareX 1-2 (2015): 19-25.

Ager , et al., "Clinical update on linezolid in the treatment of Gram-positive bacterial infections", Infection and drug resistance 5 (2012): 87-102.

Allison , et al., "Metabolite-enabled eradication of bacterial persisters by aminoglycosides", Nature 473(7346) (2011): 216-220.

American Diabetes Association , "Diagnosis and classification of diabetes mellitus", Diabetes care 27(s1) (2004): S5-S10.

American Diabetes Association , "Standards of medical care in diabetes—2010", Diabetes care 33(Supplement 1) (2010): S11-S61.

Anderson , et al., "Amphotericin forms an extramembranous and fungicidal sterol sponge", Nature chemical biology 10(5) (2014): 400-406.

Auner , et al., "Applications of Raman spectroscopy in cancer diagnosis", Cancer and Metastasis Reviews 37(4) (2018): 691-717.

Baek , et al., "Genetic alterations responsible for reduced susceptibility to vancomycin in community-associated MRSA strains of ST72", Journal of Antimicrobial Chemotherapy 72(9) (2017): 2454-2460.

Baginski , et al., "Comparative molecular dynamics simulations of amphotericin B-cholesterol/ergosterol membrane channels", Biochimica et Biophysica Acta (BBA)-Biomembranes 1567 (2002): 63-78.

Baldwin , "Structure and cooperativity of haemoglobin", Trends in Biochemical Sciences 5(8) (1980): 224-228.

Barman , et al., "Raman spectroscopy-based sensitive and specific detection of glycated hemoglobin", Analytical chemistry 84(5) (2012): 2474-2482.

Baumgart , et al., "Fluorescence probe partitioning between Lo/Ld phases in lipid membranes", Biochimica et Biophysica Acta (BBA)-Biomembranes 1768(9) (2007): 2182-2194.

Bayer , et al., "Mechanisms of daptomycin resistance in *Staphylococcus aureus*: role of the cell membrane and cell wall", Annals of the New York Academy of Sciences 1277(1) (2013): 139-158.

Belenky , et al., "Fungicidal drugs induce a common oxidative-damage cellular death pathway", Cell reports 3(2) (2013): 350-358.

Boland , et al., "Limitations of Conventional Methods of Self-Monitoring of Blood Glucose Lessons Learned from 3 days of continuous glucose sensing in pediatric patients with type 1 diabetes", Abstract 397-P and Diabetes care 24 (11) (2001): 1858-1862.

Bolard , "How do the polyene macrolide antibiotics affect the cellular membrane properties?", Biochimica et Biophysica Acta (BBA)-Reviews on Biomembranes 864(3-4) (1986): 257-304.

Bongomin , et al., "Global and multi-national prevalence of fungal diseases-estimate precision", Journal of fungi 3(4) (2017): 57.

Brown , et al., "Hidden killers: Human fungal infections", Science translational medicine 4(165) (2012): 165rv13.

Brozek-Pluska , et al., "Raman spectroscopy and imaging: applications in human breast cancer diagnosis", Analyst 137(16) (2012): 3773-3780.

Butler , et al., "Removal of dissolved oxygen from water: a comparison of four common techniques", Talanta 41 (2) (1994): 211-215.

Camden , et al., "Probing the Structure of Single-Molecule Surface-Enhanced RamanScattering Hot Spots", Journal of the American Chemical Society 130(38) (2008): 12616-12617.

Camp , et al., "High-speed coherent Raman fingerprint imaging of biological tissues", Nature photonics 8(8) (2014): 627-634.

Cegelski , et al., "The biology and future prospects of antivirulence therapies", Nature Reviews Microbiology 6(1) (2008): 17-27.

Chen , et al., "Label-free imaging of heme dynamics in living organisms by transient absorption microscopy", Analytical chemistry 90(5) (2018): 3395-3401.

Chen , et al., "Small-molecule targeting of a diapophytoene desaturase inhibits *S. aureus* virulence", Nature chemical biology 12(3) (2016): 174-179.

Cheng , et al., "Ordering of water molecules between phospholipid bilayers visualized by coherent anti-Stokes Raman scattering microscopy", Proceedings of the National Academy of Sciences 100(17) (2003): 9826-9830.

Cheng , et al., "Photoinactivation of catalase", Photochemistry and Photobiology 34(1) (1981): 125-129.

Cheng , et al., "Vibrational spectroscopic imaging of living systems: An emerging platform for biology and medicine.", Science 350(6264) (2015): 1054, aaa8870.

Cheron , et al., "Quantitative structure-activity relationships in amphotericin B derivatives", Biochemical pharmacology 37(5) (1988): 827-836.

Chiu , et al., "On the origin of the 1602 cm-1 Raman band of yeasts; contribution of ergosterol", Journal of biophotonics 5(10) (2012): 724-728.

Chong , et al., "Ground-state depletion microscopy: Detection sensitivity of single-molecule optical absorption at room temperature", The Journal of Physical Chemistry Letters 1 (23) (2010): 3316-3322.

Chuang , et al., "Resonance Raman spectra of bovine liver catalase compound 11. Similarity of the heme environment to horseradish peroxidase compound II", Journal of Biological Chemistry 264(24) (1989): 14209-14215.

(56) References Cited

OTHER PUBLICATIONS

Clatworthy, et al., "Targeting virulence: a new paradigm for antimicrobial therapy", Nature chemical biology 3(9) (2007): 541-548.
Cohen, et al., "Red cell life span heterogeneity in hematologically normal people is sufficient to alter HbA1c", The Journal of the American Society of Hematology 112(10) (2008): 4284-4291.
Costerton, et al., "Bacterial biofilms: A common cause of persistent infections", Science 284(5418) (1999): 1318-1322.
Cotero, et al., "On the role of sterol in the formation of the amphotericin B channel.", Biochimica et Biophysica Acta (BBA)-Biomembranes 1375(1-2) (1998): 43-51.
Cottarel, et al., "Combination drugs, an emerging option for antibacterial therapy.", Trends in biotechnology 25(12) (2007): 547-555.
Dai, et al., "Blue light eliminates community-acquired methicillin-resistant *Staphylococcus aureus* in infected mouse skin abrasions", Photomedicine and laser surgery 31 (11) (2013): 531-538.
Dai, et al., "Concepts and principles of photodynamic therapy as an alternative antifungal discovery platform", Frontiers in Microbiology (2012) 3, Article 120, 1-16.
Davydova, et al., "Transient absorption microscopy: Advances in chemical imaging of photoinduced dynamics", Laser & Photonics Reviews 10(1) (2016): 62-81.
De Kruijff, et al., "Polyene antibiotic-sterol interactions in membranes of Acholeplasma laidlawii cells and lecithin liposomes. III. Molecular structure of the polyene antibiotic-cholesterol complexes", Biochimica et Biophysica Acta (BBA)-Biomembranes 339(1) (1974): 57-70.
Defronzo, et al., "Type 2 diabetes mellitus.", Nature reviews: Disease primers 1 (1) (2015): 1-22.
Dickey, et al., "Different drugs for bad bugs: antivirulence strategies in the age of antibiotic resistance", Nature Reviews Drug Discovery 16(7) (2017): 457-471.
Digman, et al., "The phasor approach to fluorescence lifetime imaging analysis.", Biophysical journal 94(2) (2008): L14-L16.
Domingue, et al., "Transient absorption imaging of hemes with 2-color, independently tunable visible-wavelength ultrafast source.", Biomedical Optics Express 8(6) (2017): 2807-2821.
Dong, et al., "Pump-probe microscopy: theory, instrumentation, and applications", Spectroscopy 32(4) (2017): 2-11.
Doty, et al., "Raman spectroscopy for forensic purposes: recent applications for serology and gunshot residue analysis.", Trends in Analytical Chemistry 103 (2018): 215-222.
Dwyer, et al., "Antibiotics induce red ox-related physiological alterations as part of their lethality", Proceedings of the National Academy of Sciences 111 (20) (2014): E2100-E2109.
Enwemeka, et al., "Blue 470-nm light kills methicillin-resistant *Staphylococcus aureus* (MRSA) in vitro", Photomedicine and laser surgery 27(2) (2009): 221-226.
Feuerstein, et al., "Syngeric antibacterial effect between visible light and hydrogen peroxide on *Streptococcus mutans*", Journal of Antimicrobial Chemotherapy (2006) 57, 872-876.
Fila, et al., "Blue light treatment of *Pseudomonas aeruginosa*: Strong bactericidal activity, synergism with antibiotics and inactivation of virulence factors", Virulence 8.6 (2017): 938-958.
Finkelstein, "Aqueous pores created in thin lipid membranes by antibiotics nystatin, amphotericin Band gramicidin A: implications for pores in plasma membranes", Drugs and Transport Processes: A Symposium (1973): 241-250.
Fischer, et al., "Invited review article: Pump-probe microscopy", Review of Scientific Instruments 87(3) (2016): 031101.
Flannagan, et al., "Antimicrobial mechanisms of macrophages and the immune evasion strategies of *Staphylococcus aureus*", Pathogens 4(4) (2015): 826-868.
Flemming, et al., "Biofilms: an emergent form of bacterial life", Nature Reviews Microbiology 14(9) (2016): 563-575.
Florkowski, "HbA1c as a diagnostic test for diabetes mellitus—Reviewing the evidence", The Clinical Biochemist Reviews 34(2) (2013): 75-83.
Fluckiger, et al., "Quantitation of glycosylated hemoglobin by boronate affinity chromatography.", Diabetes 33(1) (1984): 73-76.
Franzen, et al., "Heme photolysis occurs by ultrafast excited state metal-to-ring charge transfer", Biophysical Journal 80(5) (2001): 2372-2385.
Fu, et al., "Hyperspectral imaging with stimulated Raman scattering by chirped femtosecond lasers", The Journal of Physical Chemistry B 117(16) (2013): 4634-4640.
Fu, et al., "Imaging the intracellular distribution of tyrosine kinase inhibitors in living cells with quantitative hyperspectral stimulated Raman scattering", Nature chemistry 6(7) (2014): 614-622.
Fu, et al., "Label-free in vivo optical imaging of microvasculature and oxygenation level.", Journal of biomedical optics 13(4) (2008): 040503.
Fu, et al., "Reliable cell segmentation based on spectral phasor analysis of hyperspectral stimulated Raman scattering imaging data", Analytical chemistry 86(9) (2014): 4115-4119.
Galassi, "Wavelength dependence of the time course of fluorescence enhancement and photobleaching during irradiation of ethidium bromide-stained nuclei", European journal of histochemistry: EJH 44(4) (2000): 419-432.
Gao, et al., "Dehydrosqualene desaturase as a novel target for anti-virulence therapy against *Staphylococcus aureus*.", mBio 8(5) (2017): e01224.
Gao, et al., "Transient absorption spectroscopy and imaging of individual chirality-assigned single-walled carbon nanotubes", ACS nano 6(6) (2012): 5083-5090.
Garcia-Fernandez, et al., "Membrane microdomain disassembly inhibits MRSA antibiotic resistance", Cell 171 (6) (2017): 1354-1367.
Gazi, et al., "Direct evidence of lipid translocation between adipocytes and prostate cancer cells with imaging FTIR microspectroscopy", Journal of lipid research 48(8) (2007): 1846-1856.
Geisinger, et al., "Interplay between antibiotic resistance and virulence during disease promoted by multidrug-resistant bacteria.", The Journal of infectious diseases 215 (suppl 1) (2017): S9-S17.
Ginsberg, "Factors affecting blood glucose monitoring: Sources of errors in measurement.", Journal of diabetes science and technology 3(4) (2009): 903-913.
Gough, et al., "Hydrogen peroxide: a Jekyll and Hyde signalling molecule", Cell death & disease 2.10 (2011): e213.
Grobe, et al., "Label-free imaging and spectroscopic analysis of intracellular bacterial infections.", Analytical chemistry 87(4) (2015): 2137-2142.
Guck, et al., "The optical stretcher: a novel laser tool to micromanipulate cells.", Biophysical journal 81 (2) (2001): 767-784.
Guffey, et al., "In vitro bactericidal effects of 405-nm and 470-nm blue light", Photomedicine and laser therapy 24(6) (2006): 684-688.
Guignard, et al., "Beta-lactams against methicillin-resistant *Staphylococcus aureus*", Current opinion in pharmacology 5 (5) (2005): 479-489.
Gustaffson, et al., "Three-dimensional resolution doubling in wide-field fluorescence microscopy by structured illumination", Biophysical journal 94(12) (2008): 4957-4970.
Gutierrez, et al., "Understanding and sensitizing density-dependent persistence to quinolone antibiotics", Molecular cell 68(6) (2017): 1147-1154.
Hahn, "Raman Scattering Theory", Department of Mechanical and Aerospace Engineering, University of Florida Thesis (2007).
Haka, et al., "Diagnosing breast cancer by using Raman spectroscopy", Proceedings of the National Academy of Sciences 102(35) (2005): 12371-12376.
Hamblin, et al., "Photodynamic therapy: A new antimicrobial approach to infectious disease?", Photochemical & Photobiological Sciences 3(5) (2004): 436-450.
Hampton, et al., "Inside the neutrophil phagosome: Oxidants, myeloperoxidase, and bacterial killing", Blood 92(9) (1998): 3007-3017.
Hansberg, et al., "Fungal catalases: function, phylogenetic origin and structure", Archives of biochemistry and biophysics 525(2) (2012): 170-180.

(56) References Cited

OTHER PUBLICATIONS

Haque, et al., "Clinical significance of glycated hemoglobin (HbA1c)", Anwer Khan Modern Medical College Journal 4 (1) (2013): 3-5.
Hartland, "Ultrafast studies of single semiconductor and metal nanostructures through transient absorption microscopy.", Chemical Science 1 (3) (2010): 303-309.
Herman, et al., "Underdiagnosis of peripheral neuropathy in type 2 diabetes", Diabetes care 28(6) (2005): 1480-1481.
Hess, et al., "Ultra-high resolution imaging by fluorescence photoactivation localization microscopy", Biophysical journal 91 (11) (2006): 4258-4272.
Himeno, et al., "Charge-induced phase separation in lipid membranes", Soft Matter 10(40) (2014): 7959-7967.
Hoelzel, et al., "IFCC reference system for measurement of hemoglobin A1c in human blood and the national standardization schemes in the United States, Japan, and Sweden: a method-comparison study", Clinical chemistry 50 (1) (2004): 166-174.
Hong, et al., "Antibiotic susceptibility determination within one cell cycle at single-bacterium level by stimulated Raman metabolic imaging", Analytical chemistry 90(6) (2018): 3737-3743.
Hooper, "Fluoroquinolone resistance among Gram-positive cocci", The Lancet infectious diseases 2(9) (2002): 530-538.
Huang, et al., "Breaking the diffraction barrier: Super-resolution imaging of cells.", Cell 143(7) (2010): 1047-1058.
Huang, et al., "High-speed spectroscopic transient absorption imaging of defects in graphene.", Nano Letters 18(2) (2018): 1489-1497.
Huang, et al., "Nonlinear optical microscopy of single nanostructures", Annual Review of Materials Research 43 (2013): 213-236.
Huang, et al., "Super-resolution fluorescence microscopy.", Annual review of biochemistry 78 (2009): 993-1016.
Humphreys, et al., "Combinatorial activities of ionic silver and sodium hexametaphosphate against microorganisms associated with chronic wounds", Journal of antimicrobial chemotherapy 66(11) (2011): 2556-2561.
Immergluck, et al., "Risk of skin and soft tissue infections among children found to be Staphylococcus aureus MRSA USA300 carriers", Western Journal of Emergency Medicine 18(2) (2017): 201-212.
Jabra-Rizk, et al., "Effect of farnesol on Staphylococcus aureus biofilm formation and antimicrobial susceptibility", Antimicrobial agents and chemotherapy 50(4) (2006): 1463-1469.
Jacobsen, et al., "Candida albicans dimorphism as a therapeutic target", Expert review of anti-infective therapy 10 (1) (2012): 85-93.
Jacques, "Optical properties of biological tissues: a review", Physics in Medicine & Biology 58(11) (2013): R37-R61.
Jeffrey-Smith, et al., "Candida auris: a review of the literature", Clinical microbiology reviews 31 (1) (2018): e00029-17.
Jehlicka, et al., "Potential and limits of Raman spectroscopy for carotenoid detection in microorganisms: Implications for astrobiology.", Philosophical Transactions of the Royal Society A: Mathematical, Physical and Engineering Sciences 372(2030) (2014): 20140199.
Ji, et al., "Detection of human brain tumor infiltration with quantitative stimulated Raman scattering microscopy", Science translational medicine 7(309) (2015): 309ra163.
Jo, et al., "Homogeneous immunosensor based on luminescence resonance energy transfer for glycated hemoglobin detection using upconversion nanoparticles", Analytical chemistry 88(5) (2016): 2742-2746.
Jones, et al., "Failures in clinical treatment of Staphylococcus aureus infection with daptomycin are associated with alterations in surface charge, membrane phospholipid asymmetry, and drug binding", Antimicrobial agents and chemotherapy 52(1) (2008): 269-278.
Jorgensen, et al., "Comparison of simple potential functions for simulating liquid water", The Journal of chemical physics 79(2) (1983): 926-935.
Jung, et al., "Fast detection of the metallic state of individual single-walled carbon nanotubes using a transient-absorption optical microscope", Physical review letters 105(21) (2010): 217401.
Kaatz, et al., "Efflux-mediated fluoroquinolone resistance in Staphylococcus aureus", Antimicrobial agents and chemotherapy 37(5) (1993): 1086-1094.
Kaiser, et al., "Modified HPLC-electrospray ionization/mass spectrometry method for HbA1c based on IFCC reference measurement procedure", Clinical chemistry 54(6) (2008): 1018-1022.
Kaloriti, et al., "Mechanisms underlying the exquisite sensitivity of Candida albicans to combinatorial cationic and oxidative stress that enhances the potent fungicidal activity of phagocytes", mBio 5(4) (2014): e01334-14.
Kazmierczak, et al., "Facing antibiotic resistance: Staphylococcus aureus phages as a medical tool", Viruses 6(7) (2014): 2551-2570.
Kelechava, "ANSI Z136.1-2014: Safe Use of Lasers", Blog—American National Standards Institute (2015).
Kim, et al., "A new class of synthetic retinoid antibiotics effective against bacterial persisters", Nature 556(7699) (2018): 103-107.
Kim, et al., "Endoscopic imaging using surface-enhanced Raman scattering", European Journal of nanomedicine 9 (3-4) (2017): 91-104.
Kiran, et al., "Selective Detection of HbA1c Using Surface Enhanced Resonance Raman Spectroscopy", Anal. Chem. 82 (2010): 1342-1348.
Klar, et al., "Fluorescence microscopy with diffraction resolution barrier broken by stimulated emission", Proceedings of the National Academy of Sciences 97(15) (2000): 8206-8210.
Koval, et al., "Analysis of glycated hemoglobin A1c by capillary electrophoresis and capillary isoelectric focusing", Analytical biochemistry 413(1) (2011): 8-15.
Kumar, et al., "Characterization of carotenoids in soil bacteria and investigation of their photodegradation by UVA radiation via resonance Raman spectroscopy", Analyst 140(13) (2015): 4584-4593.
Lee, et al., "Imaging chemistry inside living cells by stimulated Raman scattering microscopy", Methods 128 (2017): 119-128.
Lee, et al., "Xenon Flash Lamp Lift-Off Technology without Laser for Flexible Electronics", Micromachines 2020, 11, 953.
Lehar, et al., "Novel antibody-antibiotic conjugate eliminates intracellular S. aureus", Nature 527(7578) (2015): 323-328.
Leiter, "Type 1 diabetes genes in rats: few or many?", Diabetes 58(4) (2009): 796-797.
Lewis, et al., "Microbiology: Antibiotics right under our nose", Nature 535(7613) (2016): 501-502.
Lewis, "Persister cells", Annual review of microbiology 64 (2010): 357-372.
Lewis, "Platforms for antibiotic discovery", Nature reviews Drug discovery 12(5) (2013): 371-387.
Li, et al., "Efflux-mediated drug resistance in bacteria: An update.", Drugs 69(12) (2009): 1555-1623.
Ciao, et al., "Spectrometer-free vibrational imaging by retrieving stimulated Raman signal from highly scattered photons", Science advances 1 (9) (2015): e1500738.
Lichtman, et al., "Fluorescence microscopy", Nature methods 2(12) (2005): 910-919.
Lim, et al., "Structural basis for the Beta-lactam resistance of PBP2a from methicillin-resistant Staphylococcus aureus", Nature structural biology 9(11) (2002): 870-876.
Lipska, et al., "HbA1c and risk of severe hypoglycemia in type 2 diabetes: the Diabetes and Aging Study", Diabetes care 36(11) (2013): 3535-3542.
Liu, et al., "A cholesterol biosynthesis inhibitor blocks Staphylococcus aureus virulence", Science 319(5868) (2008): 1391-1394.
Liu, et al., "Color me bad: microbial pigments as virulence factors", Trends in microbiology 17(9) (2009): 406-413.
Liu, et al., "Label-free spectroscopic detection of membrane potential using stimulated Raman scattering.", Applied Physics Letters 106(17) (2015): 173704.
Liu, et al., "Staphylococcus aureus golden pigment impairs neutrophil killing and promotes virulence through its antioxidant activity", The Journal of experimental medicine 202(2) (2005): 209-215.
Llansola-Portoles, et al., "Electronic and vibrational properties of carotenoids: from in vitro to in vivo", Journal of The Royal Society Interface 14(135) (2017): 20170504.

(56) References Cited

OTHER PUBLICATIONS

Lockhart, et al., "Simultaneous emergence of multidrug-resistant Candida auris on 3 continents confirmed by whole-genome sequencing and epidemiological analyses", Clinical Infectious Diseases 64(2) (2017): 134-140.
MacDonald, et al., "Identifying off-target effects and hidden phenotypes of drugs in human cells", Nature chemical biology 2(6) (2006): 329-337.
MacKenzie, et al., "The post-antibiotic effect.", Journal of Antimicrobial Chemotherapy 32(4) (1993): 519-537.
Maher, et al., "Temperature-dependent anti-Stokes/Stokes ratios under surface-enhanced Raman scattering conditions", The Journal of Physical Chemistry B 110(13) (2006): 6797-6803.
Malanda, et al., "Self-monitoring of blood glucose in noninsulin-using type 2 diabetic patients: it is time to face the evidence", Diabetes care 36(1) (2013): 176-178.
Mallya, et al., "Absorption spectroscopy for the estimation of glycated hemoglobin (HbA1c) for the diagnosis and management of diabetes mellitus: A pilot study", Photomedicine and laser surgery 31 (5) (2013): 219-224.
Mandell, et al., "Catalase, superoxide dismutase, and virulence of Staphylococcus aureus. In vitro and in vivo studies with emphasis on staphylococcal-leukocyte interaction", The Journal of clinical investigation 55(3) (1975):561-566.
Mansfield, et al., "Label-free chemically specific imaging in planta with stimulated Raman scattering microscopy", Analytical chemistry 85(10) (2013): 5055-5063.
Marrink, et al., "The MARTINI force field: Coarse grained model for biomolecular simulations", The journal of physical chemistry B 111 (27) (2007): 7812-7824.
Marshall, et al., "Pigments of Staphylococcus aureus, a series of triterpenoid carotenoids", Journal of bacteriology 147(3) (1981): 900-913.
Matthews, et al., "Pump-probe imaging differentiates melanoma from melanocytic nevi.", Science translational medicine 3(71) (2011 ): 71ra15.
McAdow, et al., "Preventing Staphylococcus aureus sepsis through the inhibition of its agglutination in blood", PLoS Pathog 7(10) (2011): e1002307.
Miedema, et al., "Glycosylated haemoglobins: biochemical evaluation and clinical utility.", Annals of clinical biochemistry 21 (1) (1984): 2-15.
Milani, et al., "Carotenoids: biochemistry, pharmacology and treatment.", British journal of pharmacology 174(11) (2017): 1290-1324.
Milhaud, et al., "Interactions of the drug amphotericin B with phospholipid membranes containing or not ergosterol: new insight into the role of ergosterol.", Biochimica et Biophysica Acta (BBA)-Biomembranes 1558(2) (2002): 95-108.
Min, et al., "Imaging chromophores with undetectable fluorescence by stimulated emission microscopy", Nature 461 (7267) (2009): 1105-1109.
Mishra, et al., "Carotenoid-related alteration of cell membrane fluidity impacts Staphylococcus aureus susceptibility to host defense peptides", Antimicrobial agents and chemotherapy 55(2) (2011): 526-531.
Mishra, et al., "Why do bacteria use so many enzymes to scavenge hydrogen peroxide?", Archives of biochemistry and biophysics 525(2) (2012): 145-160.
Mohamed, et al., "Evaluation of short synthetic antimicrobial peptides for treatment of drug-resistant and intracellular Staphylococcus aureus", Scientific reports 6(1) (2016): 29707.
Mohammad, et al., "Antibacterial evaluation of synthetic thiazole compounds in vitro and in vivo in a methicillin-resistant Staphylococcus aureus (MRSA) skin infection mouse model.", PloS one 10(11) (2015): e0142321.
Mora-Duarte, et al., "Comparison of caspofungin and amphotericin B for invasive candidiasis", Journal of Medicine 34 7(25) (2002): 2020-2029.

Mosier-Boss, "Review on SERS of Bacteria", Biosensors 7.4 (2017) 51.
Mouri, et al., "Complex formation of amphotericin B in sterol-containing membranes as evidenced by surface plasmon resonance", Biochemistry 4 7(30) (2008): 7807-7815.
Muller, et al., "Daptomycin inhibits cell envelope synthesis by interfering with fluid membrane microdomains", Proceedings of the National Academy of Sciences 113(45) (2016): E7077-E7086.
Nagai, et al., "Cancer prevention from the perspective of global cancer burden patterns", Journal of thoracic disease 9 (3) (2017): 448-451.
Nakamura, et al., "Microbial resistance in relation to catalase activity to oxidative stress induced by photolysis of hydrogen peroxide", Microbiology and immunology 56(1) (2012): 48-55.
Nickerson, et al., "Diabetic complications: Current challenges and opportunities.", Journal of cardiovascular translational research 5(4) (2012): 375-379.
Oldfield, "Targeting isoprenoid biosynthesis for drug discovery: bench to bedside", Accounts of chemical research 43(9) (2010): 1216-1226.
Ozeki, et al., "Stimulated Raman hyperspectral imaging based on spectral filtering of broadband fiber laser pulses", Optics letters 37(3) (2012): 431-433.
Paavonen, et al., "Vascular endothelial growth factor receptor-3 in lymphangiogenesis in wound healing.", The American journal of pathology 156(5) (2000): 1499-1504.
Paddock, "Confocal Laser Scanning Microscopy", BioTechniques 27(5) (1999): 992-1004.
Paddock, "Principles and practices of laser scanning confocal microscopy", Molecular biotechnology 16(2) (2000): 127-149.
Pahlow, et al., "Isolation and identification of bacteria by means of Raman spectroscopy", Adv. Drug Del iv. Rev. 89 (2015): 105-120.
Parasassi, et al., "Two-photon fluorescence microscopy of laurdan generalized polarization domains in model and natural membranes", Biophysical Journal 72(6) (1997): 2413-2429.
Pathirana, et al., "Fluconazole-resistant Candida auris is susceptible to salivary histatin 5 killing and to intrinsic host defenses", Antimicrobial agents and chemotherapy 62(2) (2018): e01872-17.
Pauling, et al., "The magnetic properties and structure of hemoglobin, oxyhemoglobin and carbonmonoxyhemoglobin", Proceedings of the National Academy of Sciences 22(4) (1936): 210-216.
Peacock, et al., "Mechanisms of methicillin resistance in Staphylococcus aureus", Annual review of biochemistry 84 (2015): 577-601.
Penney, et al., "Raman Scattering Cross Sections", Nature Physical Science 235, (1972): 110-112.
Perez, et al., "Two-photon absorption", Revista Mexicana de Fiscia 49(1) (2003): 91-100.
Pettersen, et al., "UCSF Chimera—A visualization system for exploratory research and analysis", Journal of computational chemistry 25(13) (2004): 1605-1612.
Pfaller, et al., "Epidemiology of invasive candidiasis: a persistent public health problem", Clinical microbiology reviews 20(1) (2007): 133-163.
Piddock, "Multidrug-resistance efflux pumps—not just for resistance", Nature Reviews Microbiology 4(8) (2006): 629-636.
Piletic, et al., "Estimation of molar absorptivities and pigment sizes for eumelanin and pheomelanin using femtosecond transient absorption spectroscop", The Journal of Chemical Physics 131 (2009): 181106.
Potma, et al., "Detection of single lipid bilayers with coherent anti-Stokes Raman scattering (CARS) microscopy", Journal of Raman spectroscopy 34(9) (2003): 642-650.
Pradhan, et al., "Elevated catalase expression in a fungal pathogen is a double-edged sword of iron", PLoS pathogens 13(5) (2017): e1006405.
Premasiri, et al., "Characterization of the Surface Enhanced Raman Scattering (SERS) of Bacteria", J. Phys. Chem. B 1 09 (2005): 312-320.
Premasiri, et al., "he biochemical origins of the surface-enhanced Raman spectra of bacteria: a metabolomics profiling by SERS", Analytical and bioanalytical chemistry 408(17) (2016): 4631-4647.

(56) References Cited

OTHER PUBLICATIONS

Prince, et al., "Stimulated Raman scattering: from bulk to nano", Chemical reviews 117(7) (2017): 5070-5094.
Rahbar, et al., "The Discovery of Glycated Hemoglobin: A Major Event in the Study of NonenzymaticChemistry in Biological Systems", Ann. N.Y. Acad. Sci. 1043 (2005): 9-19.
Raman, et al., "A new type of secondary radiation", Nature 121 (3048) (1928): 501-502.
Rangel-Vega, et al., "Drug repurposing as an alternative for the treatment of recalcitrant bacterial infections", Frontiers in microbiology 6 (2015): 282.
Ritz, "Nephropathy in type 2 diabetes.", Journal of Internal Medicine 245 (1999): 111-126.
Robledo, et al., "Physiological role and potential clinical interest of mycobacterial pigments", IUBMB life 63(2) (2011): 71-78.
Robles, et al., "Label-free imaging of female genital tract melanocytic lesions with pump-probe microscopy: A promising diagnostic tool", Journal of lower genital tract disease 21 (2) (2017): 137-143.
Robles, et al., "Phasor analysis for nonlinear pump-probe microscopy.", Optics Express 20(15) (2012): 17082-17092.
Rust, et al., "Stochastic optical reconstruction microscopy (STORM) provides sub-diffraction-limit image resolution", Nature methods 3(10) (2006): 793-795.
Sacks, "Hemoglobin A1c in diabetes: Panacea or pointless?", Diabetes 62(1) (2013): 41-43.
Schaffer, et al., "Conjugation length dependence of Raman scattering in a series of linear polyenes: Implications for polyacetylene", The Journal of chemical physics 94(6) (1991): 4161-4170.
Schelenz, et al., "First hospital outbreak of the globally emerging Candida auris in a European hospital.", Antimicrobial Resistance & Infection Control 5(1) (2016): 35.
Schmid, et al., "Antimicrobial Effect of Visible Light—Photoinactivation of Legionella rubrilucens by Irradiation at 450. 470, and 620 nm", Antibiotics 8.187 (2019): 1-11.
Segal, "How neutrophils kill microbes", Annu. Rev. Immunol. 23 (2005): 197-223.
Sharma, et al., "SERS: Materials, applications, and the future", Materials today 15(1-2) (2012): 16-25.
Sherwani, et al., "Significance of HbA1c test in diagnosis and prognosis of diabetic patients", Biomarker insights 11 (2016): 95-104.
Shi, et al., "Optical imaging of metabolic dynamics in animals", Nature communications 9(1) (2018): 2995.
Shirshin, et al., "Formation of hemoglobin photoproduct is responsible for two-photon and single photon-excited fluorescence of red blood cells", Laser Physics Letters 15(7) (2018): 075604.
Silge, et al., "Shedding light on host niches: label-free in situ detection of Mycobacterium gordonae via carotenoids in macrophages by Raman microspectroscopy", Cellular Microbiology 17(6) (2015): 832-842.
Siqueira, et al., "Microbiology and treatment of acute apical abscesses", Clinical microbiology reviews 26(2) (2013): 255-273.
Smith, et al., "Daptomycin in combination with ceftolozane-tazobactam or cefazolin against daptomycin-susceptible and -nonsusceptible *Staphylococcus aureus* in an in vitro, hollow-fiber model", Antimicrobial agents and chemotherapy 60(7) (2016): 3970-3975.
Sokol-Anderson, et al., "Amphotericin B-induced oxidative damage and killing of Candida albicans", Journal of Infectious Diseases 154(1) (1986): 76-83.
Sopirala, et al., "Synergy testing by Etest, microdilution checkerboard, and time-kill methods for pan-drug-resistant Acinetobacter baumannii.", Antimicrobial agents and chemotherapy 54(11) (2010): 4678-4683.
Srivastava, et al., "Highly sensitive and specific detection of *E. coli* by a SERS nanobiosensor chip utilizing metallic hanosculptured thin films", Analyst 140(9) (2015): 3201-3209.
Stockel, et al., "Identification of Bacillus anthracis via Raman spectroscopy and chemometric approaches", Analytical chemistry 84(22) (2012): 9873-9880.

Stratonnikov, et al., "Photobleaching of photosensitizers applied for photodynamic therapy.", Proceedings of the SPIE 3909, Optical Methods for Tumor Treatment and Detection: Mechanisms and Techniques in Photodynamic Therapy IX (2000).
Stringari, et al., "Phasor approach to fluorescence lifetime microscopy distinguishes different metabolic states of germ cells in a live tissue", Proceedings of the National Academy of Sciences 108(33) (2011 ): 13582-13587.
Strommen, "Resonance raman spectroscopy", Journal of Chemical Education 54(8) (1977): 474-478.
Swartz, et al., "Blue-light-activated histidine kinases: Two-component sensors in bacteria", Science 317(5841) (2007): 1090-1093.
Tang, et al., "Mechanisms of Beta-lactam antimicrobial resistance and epidemiology of major community- and healthcare-associated multidrug-resistant bacteria", Advanced drug delivery reviews 78 (2014): 3-13.
Taylor, "Bacterial triterpenoids", Microbiological reviews 48(3) (1984): 181-198.
Thangamani, et al., "Repurposing ebselen for treatment of multidrug-resistant staphylococcal infections", Scientific reports 5 (2015): 11596.
Thomas, et al., "Incidence of diabetic retinopathy in people with type 2 diabetes mellitus attending the Diabetic Retinopathy Screening Service for Wales: retrospective analysis", BMJ 344 (2012): e874.
Tomb, et al., "Review of the comparative susceptibility of microbial species to photoinactivation using 380-480 nm violet-blue light", Photochemistry and photobiology 94.3 (2018): 445-458.
Tsien, "The Green Fluorescent Protein", Annu. Rev. Biochem. 67 (1998): 509-544.
Van Acker, et al., "The role of reactive oxygen species in antibiotic-induced cell death in Burkholderia cepacia complex bacteria", PloS one 11 (7) (2016): e0159837.
Van Acker, et al., "The role of reactive oxygen species in antibiotic-mediated killing of bacteria", Trends in microbiology 25(6) (2017): 456-466.
Vanommeslaeghe, et al., "CHARMM general force field (CGenFF): A force field for drug-like molecules compatible with the CHARMM all-atom additive biological force fields", Journal of computational chemistry 31 (4) (2010): 671-690.
Verkleij, et al., "Freeze-etch electron microscopy of erythrocytes, Acholeplasma laidlawii cells and liposomal membranes after the action of filipin and amphotericin B", Biochimica et Biophysica Acta (BBA)-Biomembranes 291 (2) (1973): 577-581.
Volmer, et al., "Synthesis and biological evaluation of amphotericin B derivatives", Natural product reports 27(9) (2010): 1329-1349.
Walter, et al., "Towards a fast, high specific and reliable discrimination of bacteria on strain level by means of SERS in a microfluidic device", Lab on a Chip 11.6 (2011): 1013-1021.
Wang, et al., "Antimicrobial blue light inactivation of pathogenic microbes: State of the art", Drug Resistance Updates 33-35 (2017): 1-22.
Wang, et al., "Far-field imaging of non-fluorescent species with subdiffraction resolution", Nature photonics 7(6) (2013): 449-453.
Wang, et al., "Time-lens based hyperspectral stimulated Raman scattering imaging and quantitative spectral analysis", Journal of biophotonics 6(10) (2013): 815-820.
Wangoo, et al., "Zeta potential based colorimetric immunoassay for the direct detection of diabetic marker HbA1c using gold nanoprobes", Chemical communications 46(31) (2010): 5755-5757.
Weigelt, et al., "Linezolid versus vancomycin in treatment of complicated skin and soft tissue infections", Antimicrobial agents and chemotherapy 49(6) (2005): 2260-2266.
Welsh, et al., "Survival, persistence, and isolation of theemerging multidrug-resistantpathogenic yeast *Candida auris* on a plastic health care surface", Journal of Clinical Microbiology 55(10) (2017): 2996-3005.
Weycamp, et al., "A review of the challenge in measuring hemoglobin A1c.", Journal of Diabetes Science and Technology 3(3) (2009): 439-445.
Willyard, et al., "Drug-resistant bacteria ranked", Nature News 543(7643) (2017): 15.

(56) References Cited

OTHER PUBLICATIONS

Wood, et al., "Bacterial persister cell formation and dormancy.", Applied and environmental microbiology 79(23) (2013): 7116-7121.

Yang, et al., "Exosome-encapsulated antibiotic against intracellular infections of methicillin-resistant *Staphylococcus aureus*", International Journal of Nanomedicine 13 (2018): 8095-8104.

Yao, et al., "Photoacoustic Microscopy", Laser Photon Rev. 7(5) (2013): 1-36.

Ye, et al., "Nonlinear absorption microscopy.", Photochemistry and photobiology 85(3) (2009): 631-645.

Ye, et al., "The impact of the HbA1c level of type 2 diabetics on the structure of haemoglobin", Scientific reports 6 (2016): 33352.

Yue, et al., "Cholesteryl ester accumulation induced by PTEN loss and PI3K/AKT activation underlies human prostate cancer aggressiveness", Cell metabolism 19(3) (2014): 393-406.

Zhang, et al., "Quantitative vibrational imaging by hyperspectral stimulated Raman scattering microscopy and multivariate curve resolution analysis", Analytical chemistry 85(1) (2013): 98-106.

Zhao, et al., "Detection of food borne pathogens by surface enhanced raman spectroscopy", Frontiers in microbiology 9 (2018): 1236.

"FDA 510(k) premarket notification K190938", U.S. Food and Drug Administration (Jun. 26, 2019) 7 pages.

"Written Opinion corresponding to Singapore Application No. 11202108262V dated Jun. 1, 2023".

"Office Action corresponding to Israeli Application No. 285,128 issued Mar. 31, 2024".

"Office Action corresponding to Canadian Application No. 3,128,068 dated Apr. 4, 2024".

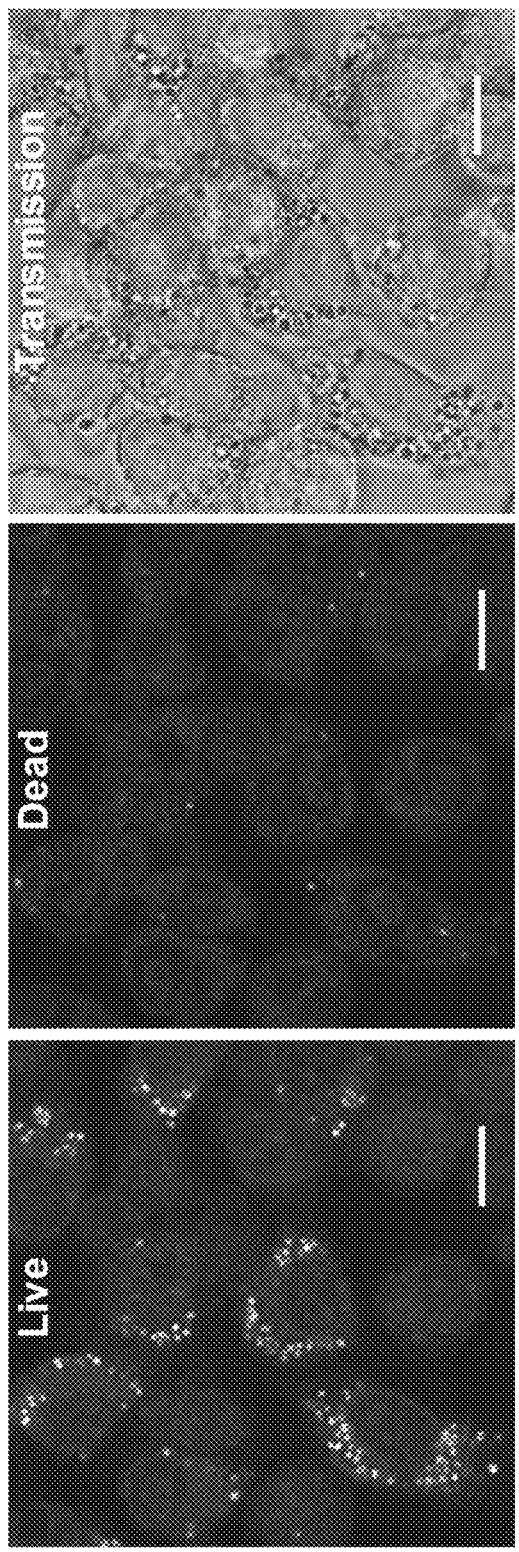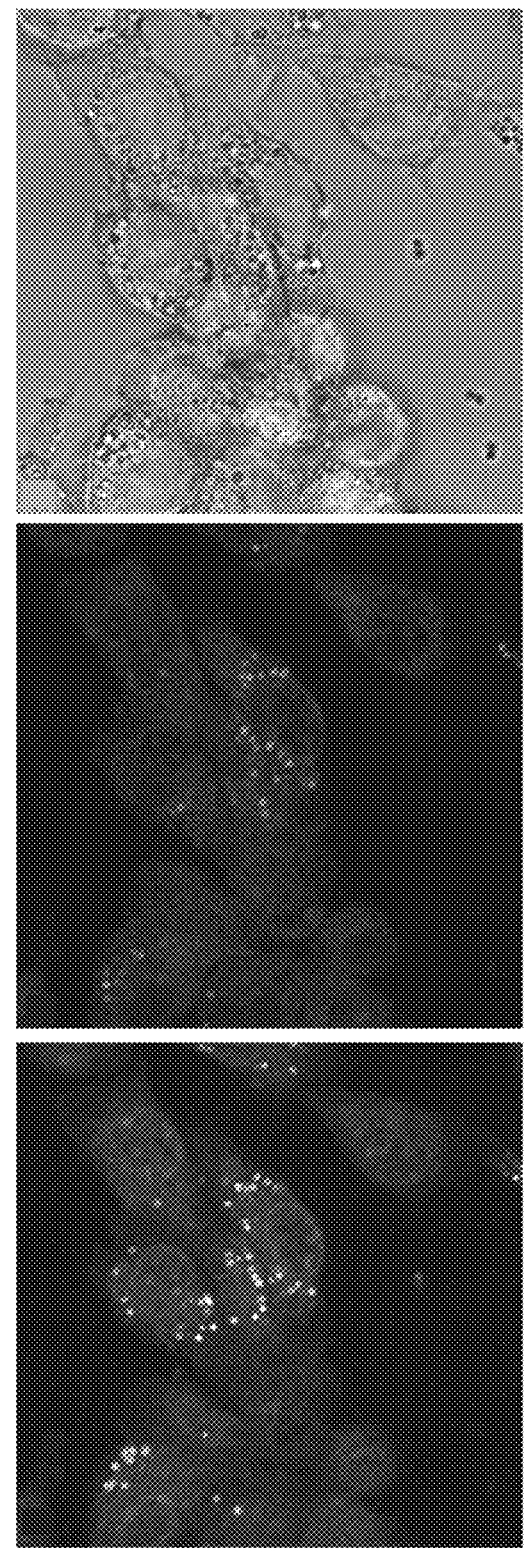

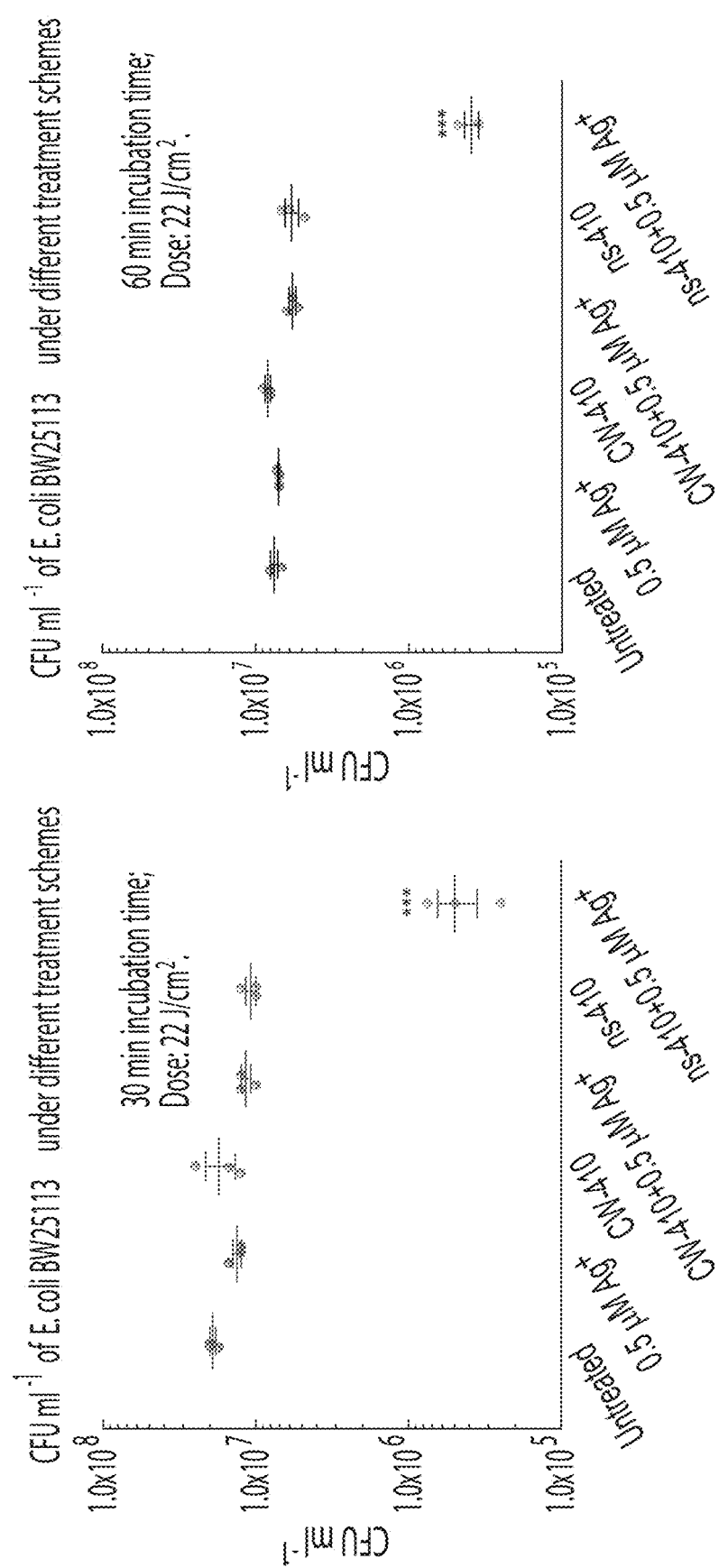

BACTERICIDAL METHODS AND COMPOSITIONS

RELATED APPLICATIONS/PATENTS

This application is a continuation of and claims priority to U.S. patent application Ser. No. 17/685,897 filed on Mar. 3, 2022, now U.S. Pat. No. 11,633,622, which is a continuation of and claims priority to U.S. patent application Ser. No. 17/387,579 filed on Jul. 28, 2021, now U.S. Pat. No. 11,298,563, which is a continuation application of and claims priority to U.S. patent application Ser. No. 17/005,807 filed on Aug. 28, 2020, now U.S. Pat. No. 11,110,296, which is a continuation of and claims priority under 35 U.S.C. § 120 of co-pending International Patent Application No. PCT/US2020/016125 filed on Jan. 31, 2020, which claims the benefit under 35 U.S.C. § 119(e) of U.S. Provisional Application Ser. No. 62/799,328 filed on Jan. 31, 2019, the contents of each of which are incorporated herein by reference in their entireties.

STATEMENT OF RIGHTS TO INVENTIONS MADE UNDER FEDERALLY SPONSORED RESEARCH

This work was supported by a National Institutes of Health Grant No. R01AI132638. The government may have certain rights to the invention.

BACKGROUND OF THE INVENTION

Antibiotic resistance kills an estimated 700,000 people each year worldwide, and studies predict that this number could rise to 10 million by 2050, if efforts are not made to curtail resistance (Willyard, C. J. N. N. The drug-resistant bacteria that pose the greatest health threats. 543, 15 (2017)). Yet, the pace of resistance acquisition from mutation in pathogens is faster than clinical introduction of new antibiotics. There is an urgent need to develop unconventional ways to combat the resistance.

SUMMARY OF THE INVENTION

The lethal effect of certain antibiotics occurs through the generation of Reactive Oxygen Species (ROS). Catalase, the ubiquitous key defense enzyme existing in most of the aerobic pathogens, is utilized to scavenge hydrogen peroxide, thus preventing downstream oxidative damage. It has now been shown that catalase can be optimally photoinactivated by blue light having a wavelength of about 400 nm to about 430 nm, and specifically, a wavelength of about 410 nm. Photoinactivation of catalase renders broad-SPECTRUM catalase-positive microbial pathogens highly susceptible to ROS-generating antimicrobials and/or immune cell attack. It has now been further determined that the antimicrobial effect of photoinactivation is significantly and unexpectedly increased upon administration of a low-concentration of $H_2O_2$ and/or a ROS-generating agent.

In one aspect, the invention provides a method of treating a tissue of a subject infected with a catalase-positive microbe, said method comprising the steps of: applying light to the tissue of the subject infected with the catalase-positive microbe at a wavelength of about 400 nm to about 430 nm, wherein the catalase is inactivated, and contacting the tissue with a composition comprising a diluted peroxide solution, thereby treating the tissue of the subject infected with the catalase-positive microbe.

In one embodiment, the wavelength is about 410 nm.

In another embodiment, the dose of the light is about 5 $J/cm^2$ to about 200 $J/cm^2$.

In yet another embodiment, the dose of the light is about 15 $J/cm^2$.

In yet another embodiment, the catalase-positive microbe is a fungal or bacterial microbe and the light is provided by a pulsed nanosecond laser.

In yet another embodiment, the catalase-positive microbe is a fungal or bacterial microbe and the light is provided by a continuous wave LED.

In yet another embodiment, the diluted peroxide solution is a hydrogen peroxide solution.

In yet another embodiment, the hydrogen peroxide solution is between about 0.03% and about 0.3% hydrogen peroxide.

In yet another embodiment, the method further comprises administering a ROS generating agent to the infected tissue of the subject.

In yet another embodiment, the ROS generating agent is tobramycin, silver cation, iodine tincture, a gold nanoparticle, methylene blue, a β-lactam antibiotic, an aminoglycoside, a fluoroquinolone, an azole, a membrane-targeting polyene antifungal or a cell-wall targeting antifungal.

In yet another embodiment, the tissue is skin, scalp or nails.

In yet another embodiment, the catalase-positive microbe is eradicated.

In another aspect, the invention provides a method of disinfecting an inanimate surface contaminated with a catalase-positive microbe, said method comprising the steps of: applying light to the inanimate surface at a wavelength of about 400 nm to about 430 nm, wherein the catalase is inactivated, and contacting the inanimate surface with a composition comprising a diluted peroxide solution, thereby disinfecting the inanimate surface.

In one embodiment, the wavelength is about 410 nm.

In another embodiment, the dose of the light is about 5 $J/cm^2$ to about 200 $J/cm^2$.

In yet another embodiment, the dose of the light is about 15 $J/cm^2$.

In yet another embodiment, the catalase-positive microbe is a fungal or bacterial microbe and the light is provided by a pulsed nanosecond laser.

In yet another embodiment, the catalase-positive microbe is a fungal or bacterial microbe and the light is provided by a continuous wave LED.

In yet another embodiment, the diluted peroxide solution is a hydrogen peroxide solution.

In yet another embodiment, the hydrogen peroxide solution is between about 0.03% and about 0.3% hydrogen peroxide.

In yet another embodiment, the method further comprises administering a ROS generating agent to the infected tissue of the subject.

In yet another embodiment, the ROS generating agent is tobramycin, silver cation, iodine tincture, a gold nanoparticle, methylene blue, a β-lactam antibiotic, an aminoglycoside, a fluoroquinolone, an azole, a membrane-targeting polyene antifungal or a cell-wall targeting antifungal.

In yet another embodiment, the inanimate surface is a material comprising metal, plastic, fabric, rubber, stone, composite surfaces or wood.

In yet another embodiment, the catalase-positive microbe is eradicated.

In yet another aspect, the invention provides a method of treating a tissue of a subject infected with a catalase-positive microbe, said method comprising the steps of: applying light from a pulsed nanosecond laser to the tissue of the subject infected with the catalase-positive microbe at a wavelength of about 400 nm to about 460 nm, wherein the catalase is inactivated, and contacting the tissue with a composition comprising a ROS generating agent, thereby treating the tissue of the subject infected with the catalase-positive microbe.

In one embodiment, the wavelength is about 410 nm.

In another embodiment, the dose of the light is about 5 J/cm$^2$ to about 200 J/cm$^2$.

In yet another embodiment, the dose of the light is about 15 J/cm$^2$.

In yet another embodiment, the catalase-positive microbe is a fungal or bacterial microbe.

In yet another embodiment, the diluted peroxide solution is a hydrogen peroxide solution.

In yet another embodiment, the hydrogen peroxide solution is between about 0.03% and about 0.3% hydrogen peroxide.

In yet another embodiment, the ROS generating agent is tobramycin, silver cation, iodine tincture, a gold nanoparticle, methylene blue, a β-lactam antibiotic, an aminoglycoside, a fluoroquinolone, an azole, a membrane-targeting polyene antifungal or a cell-wall targeting antifungal.

In yet another embodiment, the tissue is skin, scalp or nails.

In yet another embodiment, the catalase-positive microbe is eradicated.

In yet another aspect, the invention provides a method of producing a synergistic antimicrobial effect in a tissue of a subject infected with a catalase-positive microbe, said method comprising the steps of: applying light to the tissue of the subject infected with the catalase-positive microbe at a wavelength of about 400 nm to about 460 nm, wherein the catalase is inactivated, and contacting the tissue with a composition comprising a diluted peroxide solution, thereby producing the synergistic antimicrobial effect in the tissue of the subject infected with the catalase-positive microbe.

In one embodiment, the wavelength is about 410 nm.

In another embodiment, the dose of the light is about 5 J/cm$^2$ to about 200 J/cm$^2$.

In yet another embodiment, the dose of the light is about 15 J/cm$^2$.

In yet another embodiment, the catalase-positive microbe is a fungal or bacterial microbe and the light is provided by a pulsed nanosecond laser.

In yet another embodiment, the catalase-positive microbe is a fungal or bacterial microbe and the light is provided by a continuous wave LED.

In yet another embodiment, the diluted peroxide solution is a hydrogen peroxide solution.

In yet another embodiment, the hydrogen peroxide solution is between about 0.03% and about 0.3% hydrogen peroxide.

In yet another embodiment, the method further comprises administering a ROS generating agent to the infected tissue of the subject.

In yet another embodiment, the ROS generating agent is tobramycin, silver cation, iodine tincture, a gold nanoparticle, methylene blue, a β-lactam antibiotic, an aminoglycoside, a fluoroquinolone, an azole, a membrane-targeting polyene antifungal or a cell-wall targeting antifungal.

In yet another embodiment, the tissue is skin, scalp or nails.

In yet another embodiment, the catalase-positive microbe is eradicated.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

(FIG. 1A). Absorption spectra of pure catalase solution under ns-410 nm exposure. Catalase solution: 3 mg/ml, filtered with a 0.2 μm filter. (FIG. 1B). Percent of remaining active catalase after different treatment schemes (different wavelengths under the same dosage). Quantification of catalase was obtained by an Amplex Red Catalase kit. Data: Mean±standard deviation (N=3).

(FIG. 2A-2B). Percent of active catalase remained inside MRSA USA300 (FIG. 2A) and *P. aeruginosa* (FIG. 2B) after different treatment schemes (different wavelengths under the same dosage). Quantification of catalase was obtained by an Amplex Red Catalase kit. Data: Mean±standard deviation (N=3).

FIG. 5A-5B further depicts the synergistic effect between photoinactivation of catalase and low-concentration hydrogen peroxide to eliminate stationary-phase MRSA USA300 and stationary-phase *Pseudomonas aeruginosa*. FIG. 5A-5B: CFU ml-1 of stationary-phase MRSA and *P. aeruginosa* under different treatment schemes, respectively. N=3. Data: Mean±SD. ***: significant difference. p<0.001. 250 CFUs: detection of limit.

FIGS. 9A-9H depict confocal laser scanning microscopy of intracellular MRSA. (FIG. 9A-9C). Fluorescence images of intracellular live MRSA (FIG. 9A), and dead MRSA (FIG. 9B), along with the transmission images (FIG. 9C) after MRSA infecting RAW 264.7 macrophage cells for 1 hour. (FIG. 9D-9F). Fluorescence images of intracellular live MRSA (FIG. 9D), and dead MRSA (FIG. 9E), along with the transmission images (FIG. 9F) after ns-410 exposed MRSA infecting RAW 264.7 macrophage cells for 1 hour. (FIG. 9G-9H). Quantitative analysis of live/dead MRSA from the above two groups. Scalar bar=10 µm.

(FIG. 13A, 13C). $H_2O_2$-alone treated stationary-phase CASC5314 and log-phase CASC5314, respectively. (FIG. 13B, 13D). 410 nm plus $H_2O_2$ treated stationary-phase CASC5314 and log-phase CASC5314, respectively.

FIGS. 17A-17B depict the comparison between CW-410 and ns-410 to inactivate catalase and eliminate *E. coli* BW25113 by synergizing with silver cation. (FIG. 17A-17B). CFU ml$^{-1}$ of *E. coli* BW25113 after different treatment schemes: 30 min for (FIG. 17A) and 60 min for (FIG. 17B). Dose: 22 J/cm$^2$. Silver cation: 0.5 µM. Data: Mean±SEM (N=3). ***: p<0.001, significant difference. Student unpaired t-test.

DETAILED DESCRIPTION OF THE INVENTION

Definitions

Figures 1A, 1B:
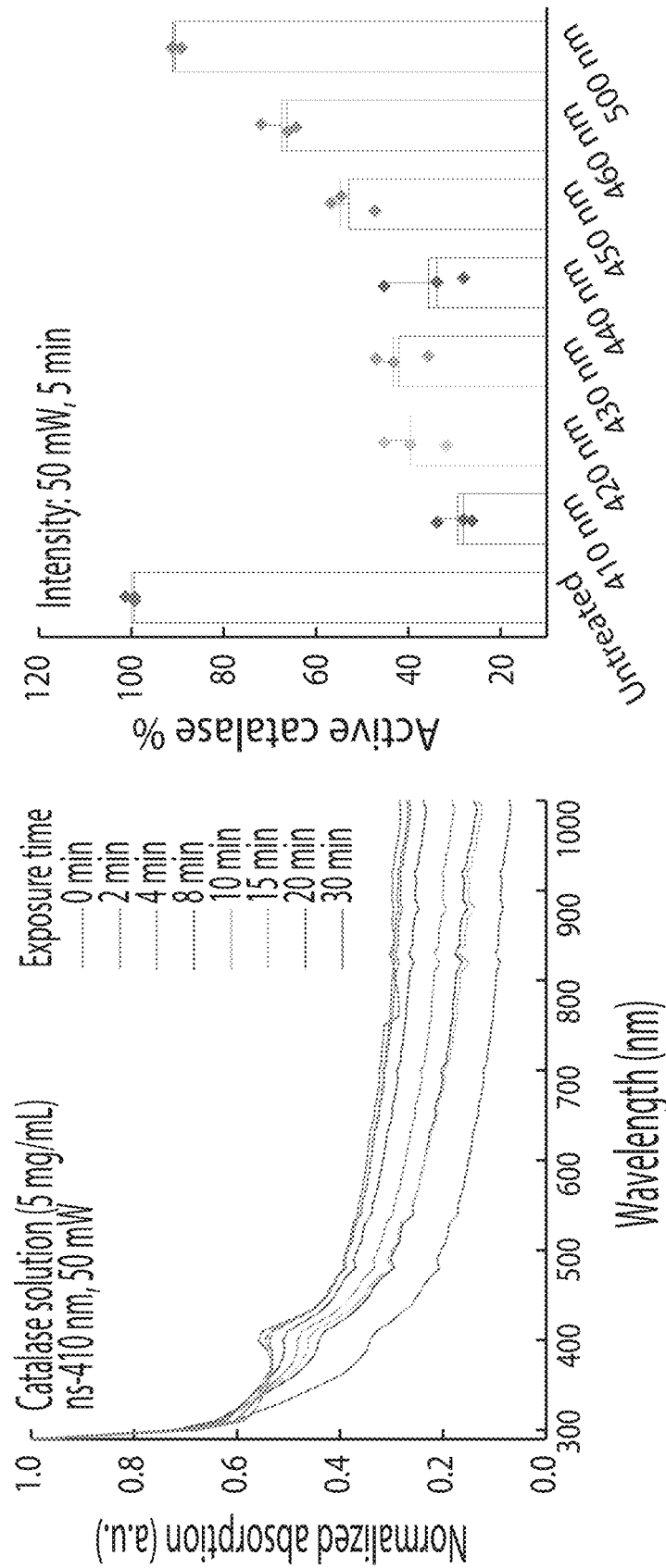
FIGS. 1A-1B depict the effect of ns-410 nm exposure on pure catalase solution.

Unless otherwise defined, all technical and scientific terms used herein have the same meaning as commonly understood by one of ordinary skill in the art to which this invention belongs. In case of conflict, the present application, including definitions will control.

As used herein, the phrase "treating an infected tissue" refers to curing, alleviating or partially arresting the clinical manifestations of the infection or its complications. Treating an infected tissue achieves a medically desirable result. In some cases, this is a complete eradication of infection. In other cases, it is an improvement in the symptoms of the infection.

A "ROS-generating agent" is any biological or chemical agent that produces Reactive Oxygen Species (ROS). ROS-generating agents as defined herein, exclude exogenous photosensitizer agents that have been light-activated. A "photosensitizer" is a chemical compound, or a biological precursor thereof, that produces a phototoxic or other biological effect on biomolecules upon photoactivation.

A "subject" is a vertebrate, including any member of the class mammalia, including humans, domestic and farm animals, and zoo, sports or pet animals, such as mouse, rabbit, pig, sheep, goat, cattle and higher primates.

A "microbe" is a multi-cellular or single-celled microorganism, including bacteria, protozoa, and some fungi and algae. The term microbe, as used herein, includes pathogenic microorganisms such as bacterium, protozoan, or fungus.

The term "inanimate surface" refers any non-living surface.

The term "disinfecting" refers to destroying or eliminating pathogenic microorganisms that cause infections.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. A range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). For example, the wavelengths from about 400 nm to about 460 nm include the wavelengths 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 554, 455, 456, 457, 458, 459 and 460 nms. The light from about 5 J/cm$^2$-to about 200 J/cm$^2$ includes 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 J/cm$^2$.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Compositions and Methods of the Invention

Hydrogen peroxide ($H_2O_2$) is continuously produced inside microbes from autoxidation of the redox enzyme, and it diffuses quickly into the intracellular environment, causing an acutely detrimental effect (e.g. lipid peroxidation, DNA and protein damage) as a result of the Fenton reaction:

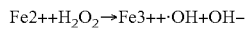

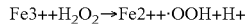

Photoinactivation of catalase creates potent antimicrobial effects due to a lethal accumulation of ROS. Photoinactivation of catalase further assists immune cells to eliminate intracellular pathogens. Neutrophils and macrophages are highly motile phagocytic cells that serve as the first line of defense of the innate immune system (Segal, A. W., Annu Rev Immunol 23, 197-223, doi:10.1146/annurev.immunol.23.021704.115653 (2005)). These cells play an essential role in providing resistance to bacterial and fungal infections through releasing ROS burst (e.g., superoxide, hydroxyl radicals, and singlet oxygen (Hampton, M. B., Blood 92, 3007-3017 (1998)). However, pathogens possess an array of elaborate strategies to invade and survive inside neutrophils or macrophages, thus acting as the 'Trojan horses' responsible for further dissemination and recurrent infections (Lehar, S. M. et al. Nature 527, 323-328 (2015)). Catalase, which is encoded by gene, katA, confers indispensable resistance for antimicrobial agents or reactive oxygen species released by immune cells (Flannagan, R., Pathogens 4, 826-868 (2015)). Photoinactivation of catalase assists macrophage and neutrophils to reduce the intracellular and extracellular bacterial burden.

In conducting the methods of the present invention, photoinactivation of catalase is preferably conducted with light having a wavelength of about 400 nm to about 430 nm, in combination with administration of a low-concentration peroxide solution and/or an ROS generating agent. Methods of the invention exclude the use of exogenous photosensitizing agents that have been activated by light.

Peroxide solutions include, but are not limited to solutions containing hydrogen peroxides, metal peroxides, and organic peroxides. Hydrogen peroxides include, but are not limited to, peroxy acids, peroxymonosulfuric acid, peracetic acid, peroxydisulfuric acid, peroxynitric acid, peroxynitrous acid, perchloric acid, and phthalimidoperoxycaproic acid. Metal peroxides include but are not limited to ammonium periodate, barium peroxide, sodium peroxide, sodium perborate, sodium persulfate, lithium peroxide, magnesium peroxide, magnesium perchlorate and zinc peroxide. Organic peroxides include but are not limited to acetone peroxide, acetozone, alkenyl peroxide arachidonic acid 5-hydroperoxide, artelinic acid, artemether, artemisinin, artemotil, arterolane, artesunate, ascaridole, benzoyl peroxide, bis(trimethylsilyl) peroxide, tert-butyl hydroperoxide tert-butyl peroxybenzoate, CSPD ([3-(1-chloro-3'-methoxyspiro[adamantane-4,4'-dioxetane]-3'-yl)phenyl] dihydrogen phosphate), cumene hydroperoxide, di-tert-butyl peroxide, diacetyl peroxide, diethyl ether peroxide, dihydroartemisinin, dimethyldioxirane, 1,2-dioxane, 1,2-dioxetane, 1,2-dioxetanedione, dioxirane, dipropyl peroxydicarbonate, ergosterol peroxide, hexamethylene triperoxide diamine, methyl ethyl ketone peroxide, nardosinone, paramenthane hydroperoxide, perfosfamide, peroxyacyl nitrate, peroxyacyl nitrates, prostaglandin h2, 1,2,4-trioxane, and verruculogen. Other peroxides include, potassium peroxydisulfate, bis(trimethylsilyl) peroxide ($Me_3SiOOSiMe_3$), phosphorus oxides, ammonium peroxide, copper(II) peroxide, sodium peroxide, cobalt(II) peroxide, mercury(I) peroxide, iron(II) peroxide potassium peroxide, copper(I) peroxide, rubidium peroxide, cesium peroxide, iron(III) peroxide, beryllium peroxide, magnesium peroxide, nickel (II) peroxide, cadmium peroxide, barium peroxide, benzoyl peroxide, calcium peroxide, diacetyl peroxide, cesium superoxide, lead(IV) peroxide, lithium peroxide, gallium(II) peroxide, chromium(III) peroxide, mercury(II) peroxide, gold(I) peroxide, strontium peroxide, zinc peroxide, potassium superoxide, and chromium(VI) peroxide.

In other specific embodiments, the diluted peroxide solution is a hydrogen peroxide solution formulated with between about 0.030% and about 0.3% hydrogen peroxide (which converts to about 8.8 mM to about 88 mM hydrogen peroxide).

Photoinactivation of catalase and administration of the peroxide solution can also be provided in combination with ROS generating agents including antibiotics, such as tobramycin. Other ROS generating agents include, but are not limited to, silver cation, iodine tincture, gold nanoparticles, methylene blue (non-photoactivated), β-lactam antibiotics, aminoglycosides, fluoroquinolones, antifungal azoles, membrane-targeting polyene antifungals, such as amphotericin B, and cell-wall targeting antifungals, such as caspofungin.

Typically following photoinactivation, the peroxide solution can be administered to the site of the infection for a duration of about 10 to about 30 minutes. In alternate embodiments, the peroxide solution, the ROS generating agent and/or the photoinactivating light can be administered concomitantly or sequentially to the site of infection. For example, in specific embodiments, the ROS-generating agent is administered prior to photoinactivation of catalase. In other specific embodiments, the ROS-generating agent is administered after the photoinactivation of catalase. Preferably, the peroxide solution is topically administered (e.g., as a liquid or a spray). Administration of the ROS generating agent can be according to all modes of local or systemic administration known in the art.

In one embodiment, methods of the invention comprising photoinactivation of catalase are directed to an infected external tissue of a subject, including, but not limited to, skin, hair and nails. In other embodiments, internal tissues, such as gastrointestinal organs or cavities (oral, vaginal or nasal cavities), may be targeted as well.

Peroxide solutions and/or ROS generating agents can be administered alone or as a component of a pharmaceutical formulation. The compounds may be formulated for administration, in any convenient way for use in human or veterinary medicine. Wetting agents, emulsifiers and lubricants, such as sodium lauryl sulfate and magnesium stearate, as well as coloring agents, release agents, and preservatives can also be present in the compositions.

Pharmaceutical formulations of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration, e.g., intradermal.

The formulations can include a pharmaceutically acceptable carrier. The amount of active ingredient which can be combined with a carrier material to produce a single dosage form will generally be that amount of the compound which produces a therapeutic effect. Formulations of the invention can be administered parenterally, intraperitoneally, subcutaneously, topically, orally (e.g., the ROS generating agent) or by local administration, such as by aerosol or transdermally. Formulations can be administered in a variety of unit dosage forms depending upon the severity of the infection or the site of the infection and the degree of illness, the general medical condition of each patient, the resulting preferred method of administration and the like. Details on techniques for formulation and administration of pharmaceuticals are well described in the scientific and patent literature, see, e.g., the latest edition of Remington's Pharmaceutical Sciences, Maack Publishing Co, Easton Pa. ("Remington's").

Pharmaceutical formulations of this invention can be prepared according to any method known to the art for the manufacture of pharmaceuticals. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

In practicing this invention, the pharmaceutical formulations can be delivered transdermally, by a topical route, formulated as applicator sticks, solutions, suspensions, emulsions, gels, creams, ointments, pastes, jellies, paints, powders, and aerosols. In specific embodiments, delivery can be mediated by a transdermal patch, bandage or dressing impregnated with compositions comprising the peroxide solution and/or ROS generating agent. Sustained release can be provided by transdermal patches, for slow release at the site of infection.

The amount of pharmaceutical formulation adequate to reduce or eradicate pathogenic microbes is a therapeutically effective dose. The dosage schedule and amounts effective for this use, i.e., the dosing regimen, will depend upon a variety of factors, including the stage of the infection, the severity of the infection, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of pharmaceutical formulations of the invention can be given depending on for example: the dosage and frequency as required and tolerated by the patient, the persistence of infection, or lack thereof, after each administration, and the like. The formulations should provide a sufficient quantity of peroxide solution to effectively treat, prevent or ameliorate the infection.

Methods of the invention target catalase positive microbes which are associated with, or may give rise to, infection. Both Gram-negative and Gram-positive bacteria serve as infectious pathogens in vertebrate animals. Such catalase positive Gram-positive bacteria include, but are not limited to, *Staphylococci* species. Catalase positive Gram-negative bacteria include, but are not limited to, *Escherichia coli*, *Pasteurella* species, *Pseudomonas* species (e.g., *P. aeruginosa*), and *Salmonella* species. Specific examples of infectious catalase positive bacteria include but are not limited to, *Helicobacter pylori, Borelia burgdorferi, Legionella pneumophilia, Mycobacteria* species (e.g. *M. tuberculosis* complex, *M. avium* complex, *M. gordonae* clade, *M. kansasii* clade, *M. nonchromogenicum/terrae* clade, Mycolactone-producing mycobacteria, *M. simiae* clade, *M. abscessus* clade, *M. chelonae* clade, *M. fortuitum* clade, *M. mucogenicum* clade, *M. parafortuitum* clade, *M. vaccae* clade, *M. ulcerans, M. vanbaalenii, M. gilvum, M. bovis, M. leprae, M. spyrl, M. kms, M. mcs, M. jls, M. intracellulare,* and *M. gordonae*), *Acinetobacter baumannii, Staphylococcus aureus, Neisseria gonorrhoeae, Neisseria meningitidis, Listeria monocytogenes,* pathogenic *Campylobacter* species, *Haemophilus influenzae, Bacillus antracis, Corynebacterium diphtheriae, corynebacterium* species, *Erysipelothrix rhusiopathiae, Chlamydia trachomatis, Clostridium perfringers, Clostridium tetani, Klebsiella pneumoniae, Pasteurella multocida, Bacteroides* species, *Fusobacterium nucleatum, Treponema pallidium, Treponema pertenue, Leptospira, Rickettsia,* and *Actinomyces israelii. Mycoplasma* and *Chlamydia* species.

Examples of catalase positive fungi include, but are not limited to, *Aspergillus fumigatus, Cryptococcus neoformans, Histoplasma capsulatum, Coccidioides immitis, Blastomyces dermatitidis, Candida glabrata, Candida tropicalis, Candida parapsilosis,* and other catalase-positive *Candida* spp. *Candida auris,* and *Trichophyton rubrum.*

The light for photoactivation of catalase can be produced and delivered to the site of infection by any suitable means known in the art.

While it has now been determined that the antimicrobial effect of photoinactivation is significantly and unexpectedly increased upon administration of a low-concentration of $H_2O_2$ and/or a ROS-generating agent, the antimicrobial effectiveness is also significantly improved when the light is provided by a pulsed nanosecond laser compared to continuous wavelength LED. Accordingly, in specific embodiments, the light source is a is a pulsed nanosecond laser. Pulsed operation of lasers refers to any laser not classified as continuous wave, so that the optical power appears in pulses of some duration at some repetition rate. Nanosecond laser families can range from the UV to the IR with wavelengths up to 1064 nm, repetition rates up to 2 kHz, and pulse energy up to 20 mJ. Photoinactivation of catalase can be conducted with light having a wavelength of about 400 nm to about 460 nm. In specific embodiments, the wavelength is about 400 nm to about 430 nm, applied at a dosage of about 5 $J/cm^2$-to about 200 $J/cm^2$, and in other specific embodiments, about 14 $J/cm^2$ to about 32 $J/cm^2$. In other specific embodiments, the pulse duration is about 5 nanoseconds. Light delivered in this range by a pulsed nanosecond laser is clinically advantageous because thermal damage is minimal, temporary or otherwise non-existent. In more specific embodiments, the wavelength is 410 nm (delivered using about 15 $J/cm^2$), applied by a pulsed nanosecond laser according to methods known in the art for operation of such lasers.

Exposure times range from about 5 to about 10 minutes in length, and can be repeated weekly as needed, for example, about twice per week for several months. In clinical applications, patients may receive treatment for between one to 3 months or longer as determined by the practicing physician.

In other embodiments, photoactivating light can be delivered to the site of infection through various optical waveguides, such as an optical fiber or implant. In some embodiments, the photoinactivating light is delivered by optical fiber devices that directly illuminate the site of infection. For example, the light can be delivered by optical fibers threaded through small gauge hypodermic needles. In addition, light can be transmitted by percutaneous instrumentation using optical fibers or cannulated waveguides. For open surgical sites, suitable light sources include broadband conventional light sources, broad arrays of LEDs, and defocused laser beams. The light source can be operated in the Continuous Wave (CW) mode. Photoinactivation of catalase is preferably conducted with light having a wavelength of about 400 nm to about 430 nm and a dosage of about 5 $J/cm^2$-to about 200 $J/cm^2$, and in specific embodiments, about 14 $J/cm^2$ to about 32 $J/cm^2$ In other specific embodiments, the wavelength is 410 nm (delivered using about 15 $J/cm^2$), applied by a CW LED according to methods known in the art for operation of such LED sources. Exposure times range from any light source range from about 5 to about 10 minutes in length.

In other embodiments of the invention, the photoinactivation of catalase is performed on an inanimate surface including but not limited to metal, plastic, fabric, rubber, stone, composite surfaces or wood. In specific embodiments, the inanimate surface comprises objects such as instruments, catheters, medical and military equipment, furniture, handrails, textiles, fixtures such as sinks and plumbing materials, building materials, industrial or electronic equipment, and food product or food processing equipment. Photoinactivation of catalase on inanimate surfaces is preferably conducted with light having a wavelength of about 400 nm to about 430 nm, and in combination with administration of a solution having a low-concentration of a peroxide. In specific embodiments, the wavelength is 410 nm (delivered at 15 $J/cm^2$), applied by a pulsed nanosecond laser. Exposure times range from about 5 to about 10 minutes in length.

The following examples are put forth for illustrative purposes only and are not intended to limit the scope of what the inventors regard as their invention.

EXAMPLES

The following materials and methods were employed throughout Examples 1.-4.

Bacterial strains: *Enterococcus faecalis* NR-31970, *Enterococcus faecalis* HM-325, *Escherichia coli* BW 25113, *Escherichia coli* ATCC 25922. *Klebsiella pneumoniae* ATCC BAA 1706. *Klebsiella pneumoniae* ATCC BAA 1705. *Salmonella enterica* ATCC 70720. *Salmonella enterica* ATCC 13076. *Acinetobacter baumannii* ATCC BAA 1605. *Acinetobacter baumannii* ATCC BAA-747. *Pseudomonas aeruginosa* ATCC 47085 (PAO-1). *Pseudomonas aeruginosa* 1133. *Pseudomonas aeruginosa* ATCC 15442. *Pseudomonas aeruginosa* ATCC 9027.

Quantitation of catalase by Amplex red catalase kit: Quantification of catalase both from the pure catalase solution and bacteria was achieved by a fluorescent amplex red catalase kit. 25 μl of analyte were incubated with 25 μl (40 μM of $H_2O_2$) for 30 min at room temperature. Then 50 μl of working solution (100 μM Amplex Red reagent containing 0.4 U/ml horseradish peroxidase) were added to the abovementioned mixture, and the subsequent mixture were incubated for another 30-60 min in the dark. After that, the fluorescence was recorded at an emission of 590 nm when excited at 560 nm.

Resonance Raman spectrum of dried catalase film: Catalase was measured by its Raman peaks at around 1300-1700 cm-1 measured by resonance Raman spectroscopy (1221, LABRAM HR EVO, Horiba) with a 40×objective (Olympus) and an excitation wavelength of 532 nm. Samples (dried 'coffee ring' were sandwiched between two glass cover slides (48393-230, VWR international) with a spatial distance of ~80 μm. To study the photoinactivation (by a continuous-wave LED), the same samples were measured after each laser irradiation.

CFU experiments to test the potential synergy between photoinactivation of catalase and $H_2O_2$: Overnight-cultured bacteria was centrifuged, the supernatant was discarded, and the pellet was resuspended with the same amount of PBS. The laser source used in the study is nanosecond (ns) pulsed OPO laser purchased from OPOTEK Inc, model number as Opolette HE355 LD, having the following key specifications: wavelength range, 410-2400 nm; pulse repetition rate, 20 Hz; maximum pulse energy at 460 nm, 8 mJ; pulse duration, 5 nanosecond; spectral linewidth, 4-6 cm-1; and pulse-to-pulse stability, <5%. For each bacterial strain there were four groups: untreated one, ns-410 nm-treated group, $H_2O_2$ (22 or 44 mM)-treated group, ns-410 nm plus $H_2O_2$ (22 or 44 mM)-treated group. Dose for ns-410 nm exposure was 15 $J/cm^2$. $H_2O_2$ was incubated with bacteria for 30 min at 37° C. with the shaking speed of 200 rpm. After incubation, bacterial burden from each group was serial diluted, inoculated onto TSA plates, then counted by enumeration of these plates.

CFU experiments to test the potential synergy between photoinactivation of catalase and ROS-generating antibiotics: Overnight-cultured bacteria was centrifuged, and then the supernatant was discarded and re-suspended with the same amount of fresh TSB. Then prior to any treatments, the above solution was incubated with antibiotics (10 μg/ml) for 1 hour. For each bacterial strain, four groups were tested: untreated one, ns-410 nm-treated group, antibiotic (2 μg/ml)-treated group, ns-410 nm plus antibiotic (2 μg/ml)-treated group. Dose for ns-410 nm exposure was 15 J/cm2. Antibiotic was incubated with bacteria for up to 6 hours at 37° C. with the shaking speed of 200 rpm. At each time interval, bacterial burden from each group was serial diluted, inoculated onto TSA plates, then counted by enumeration of these plates.

Confocal imaging of intracellular bacteria assay: As described elsewhere (Yang, X., et al. International journal of nanomedicine 13, 8095 (2018)), murine macrophage cells (RAW 264.7) were cultured in DMEM supplemented with 10% FBS at 37 degrees C. with CO2 (5%). Cells were exposed to MRSA USA300 or *Salmonella enterica* (with/without ns-410 nm exposure) at a multiplicity of infection (MOI) of approximately 100:1 at serum-free DMEM medium. 1 or 2-hour post-infection, RAW 264.7 cells were washed with gentamicin (50 μg/mL, for one hour) to kill extracellular bacteria in DMEM+10% FBS. After that, RAW 264.7 cells were washed with gentamicin (50 μg/mL) and subsequently lysed using 0.1% Triton-X 100 for 3 min. After membrane permeabilization, infected RAW 264.7 cells were stained with Live/Dead stain for 15 min, then samples were fixed in 10% formalin for 10 min prior confocal imaging.

Example 1: Pulsed Blue Laser Effectively Inactivates Pure Catalase and Catalase from Bacteria Pure catalase solution (bovine liver catalase, 3 mg/ml in the PBS) was prepared in PBS using a protocol previously published to examine the effect of 410-nm exposure on the absorption spectrum of catalase solution (Cheng, L., Photochemistry and Photobiology 34, 125-129 (1981)). Catalase shows a pronounced absorption at around 410 nm, and its absorption at this wavelength gradually decreases as the 410-nm exposure elongates (FIG. 1a). This suggests that the secondary structure of catalase might be changed, especially in the active heme-containing domain. In addition, this photoinactivation effect was examined by an Amplex Red Catalase kit at different wavelengths (FIG. 1b). The photoinactivation trend is similar to the absorption spectrum of catalase, with the 410 nm being the most effective, where 5-min exposure depleted ~70% active catalase.

Figures 2A, 2B:
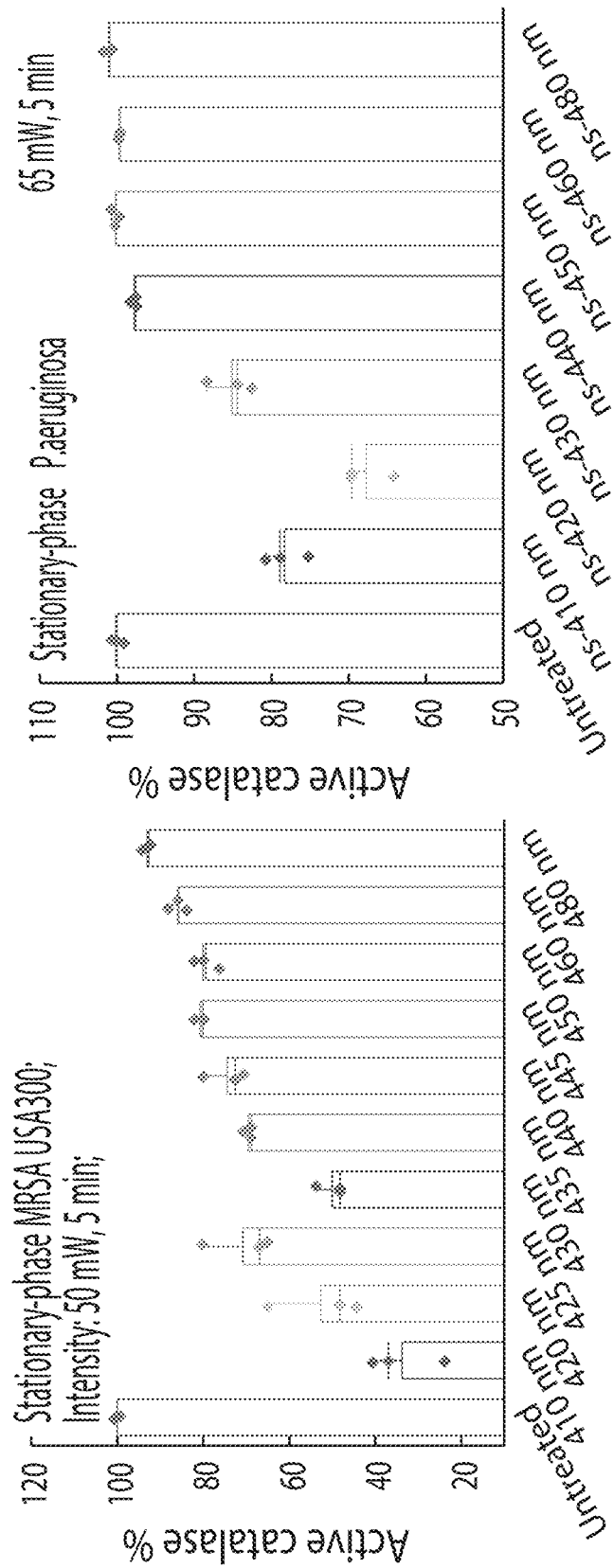
FIGS. 2A-2B depict the effect of ns-410 nm exposure on active catalase percentages from MRSA USA300 and *P. aeruginosa*.

Since most of the aerobic bacteria and facultative anaerobes express catalase (Mishra, S. & Imlay, J. Arch Biochem Biophys 525, 145-160, doi:10.1016/j.abb.2012.04.014 (2012)), whether one could photoinactivate catalase in situ from the catalase-positive bacteria was examined. MRSA USA300 and *P. aeruginosa* (PAO-1) were selected as the representative for Gram-positive and Gram-negative bacteria, respectively. Noteworthy, catalase from both MRSA USA300 (FIG. 2a) and *P. aeruginosa* (FIG. 2b) were photoinactivated by blue light exposure region, especially 410-nm exposure. The dose utilized was about 15 J/cm2, well below the ANSI safety limit of 200 $J/cm^2$, and the specimens were stationary-phase cultured bacteria (~108 cells/ml). ANSI is the American National Standard for Safe Use of Lasers, see ANSI Z136.1, Laser Institute of America 2014.

Figure 3:
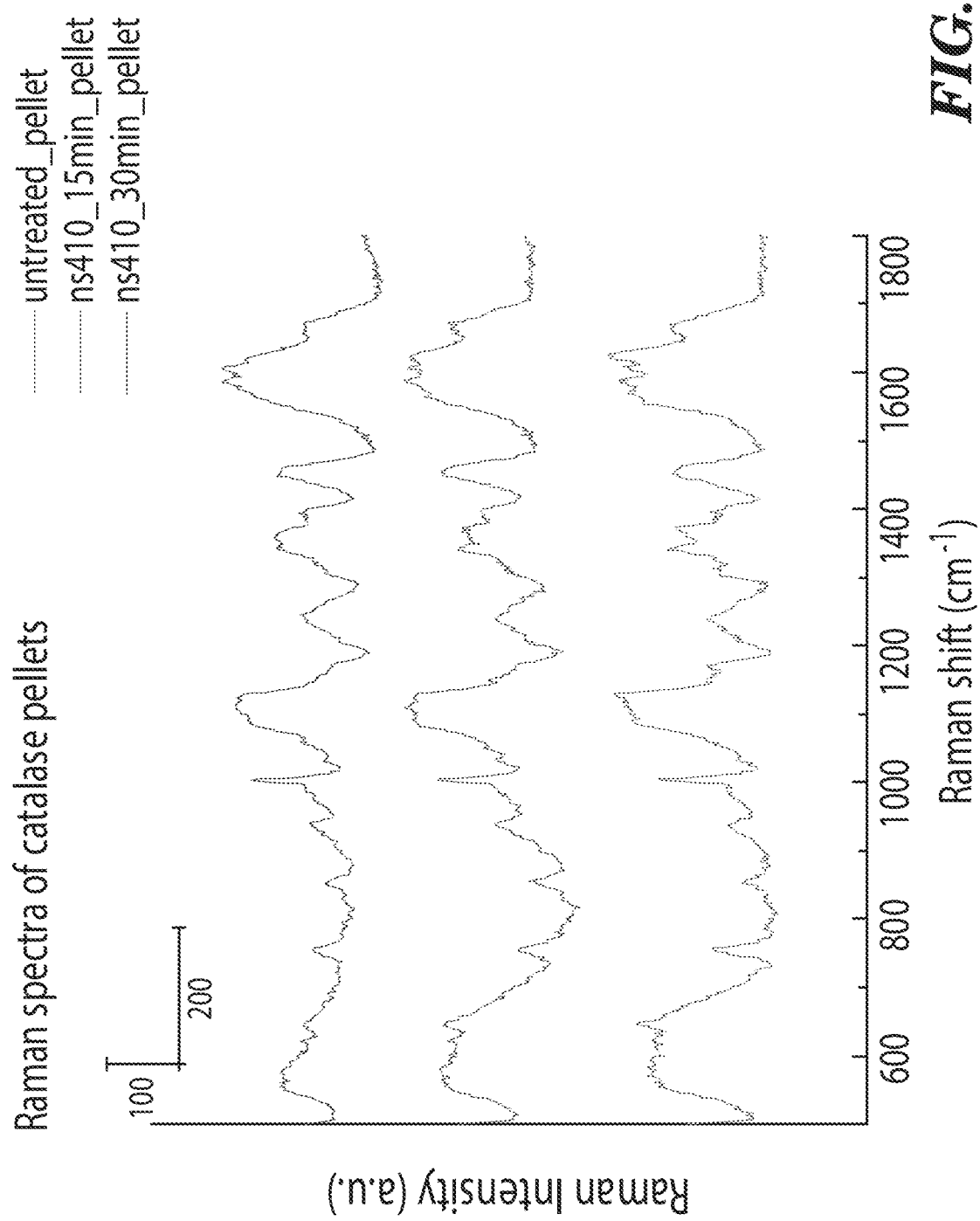
FIG. 3 depicts Resonance Raman spectra of bovine liver catalase powder with and without 410 nm exposure. 410 nm dose: 250 mW/cm2. Raman spectrum acquisition time: 25 s. 532 nm excitation. Data: Mean±SD from five spectra.

To further understand how 410 nm exposure could cause the structural change of catalase, Resonant Raman spectroscopy was performed to capture the Raman signature of dried catalase film (FIG. 3). Apparently, 410 nm exposure significantly drops the Raman intensity at 750 $cm^{-1}$, and the Raman bands ranging from 1300 $cm^{-1}$ to 1700 $cm^{-1}$, which are typical vibrational bands of heme ring from catalase (Chuang, W.-J., Heldt, J. & Van Wart, H. J. J. o. B. C. Resonance Raman spectra of bovine liver catalase compound II. Similarity of the heme environment to horseradish peroxidase compound II. 264, 14209-14215 (1989)). These data further consolidate the fact that 410 nm exposure could cause structural change of catalase.

Figures 4A, 4B, 4C:
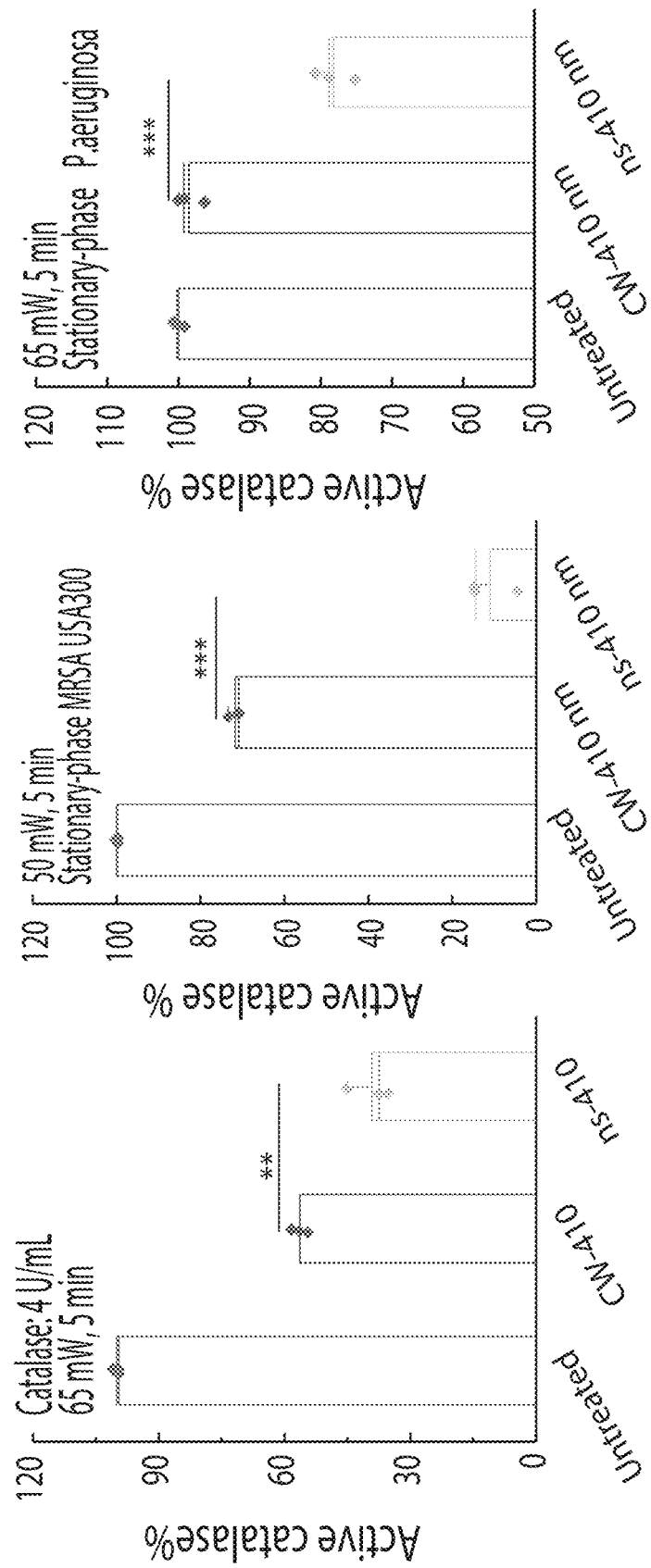
FIGS. 4A-4C depict the comparison between ns-410 nm and CW-410 nm exposure on the catalase photoinactivation effect from pure catalase solution (FIG. 4A), catalase from MRSA USA300 (FIG. 4B), and catalase from *P. aeruginosa* (FIG. 4C). Quantification of catalase was obtained by an Amplex Red Catalase kit. Data: Mean±standard deviation (N=3). Student unpaired t-test, *: p<0.001; : p<0.01.

In addition, the efficacy between ns-410 nm and CW-410 nm to inactivate catalase was compared. ns-410 nm is significantly more effective both in the pure solution form (FIG. 4a), or from MRSA USA300 (FIG. 4b) and *P. aeruginosa* (FIG. 4c) compared to CW-410 nm. Moreover, ns-410 exposure eliminates the necessity of heating tissue during future clinical study.

Figure 5A:
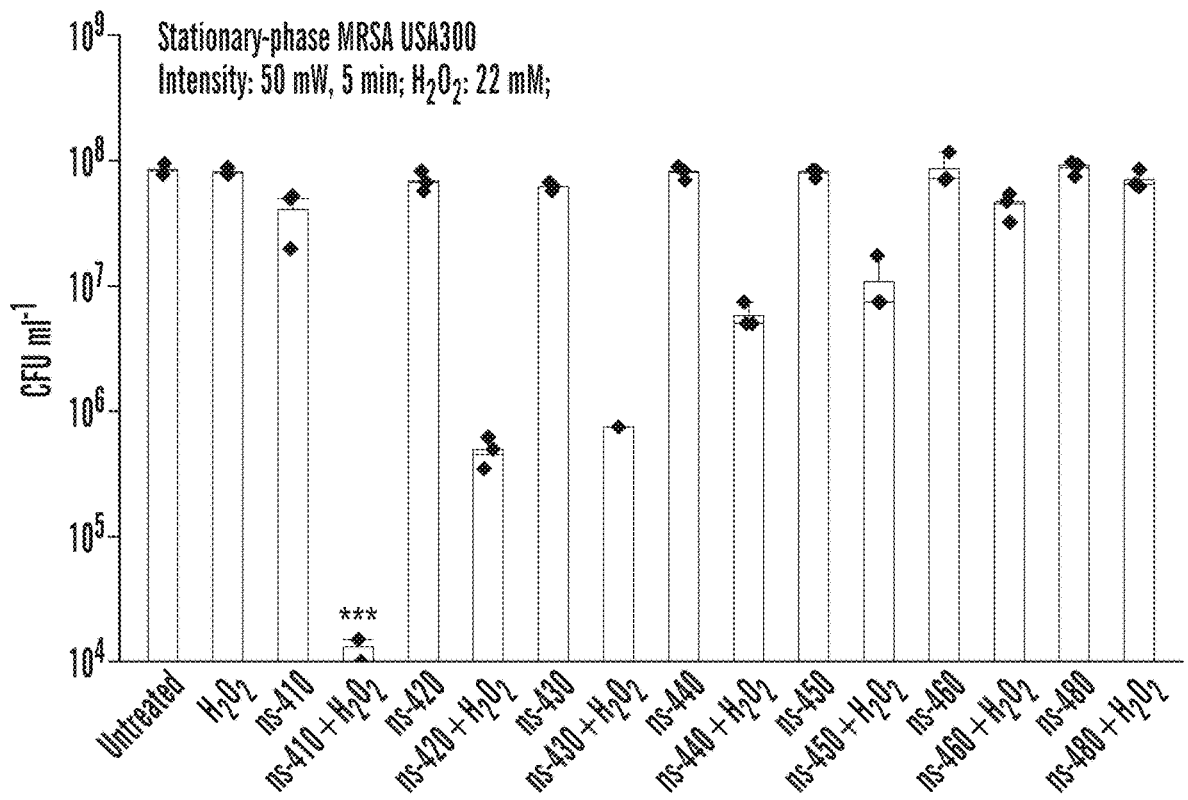
FIGS. 5A-5C depict CFU ml-1 of stationary-phase MRSA USA300 methicillin-resistant *Staphylococcus aureus* (FIG. 5A), *Pseudomonas aeruginosa* (FIG. 5B), and *Salmonella enterica* (FIG. 5C) under the treatment of 22 mM $H_2O_2$ with/without the combination with various light exposure. Data: Mean±standard deviation (N=3). Student unpaired t-test, *: p<0.001; : p<0.01. 250 CFUs: limit of detection.
Figure 5B:
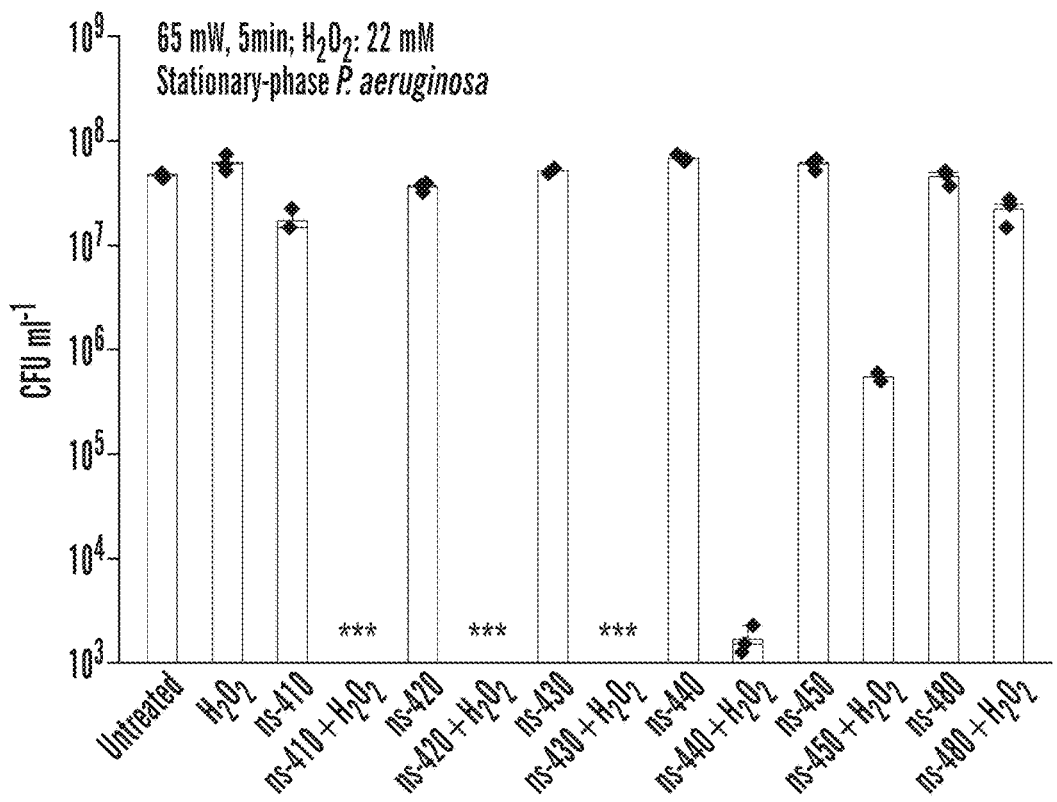
Figure 5C:
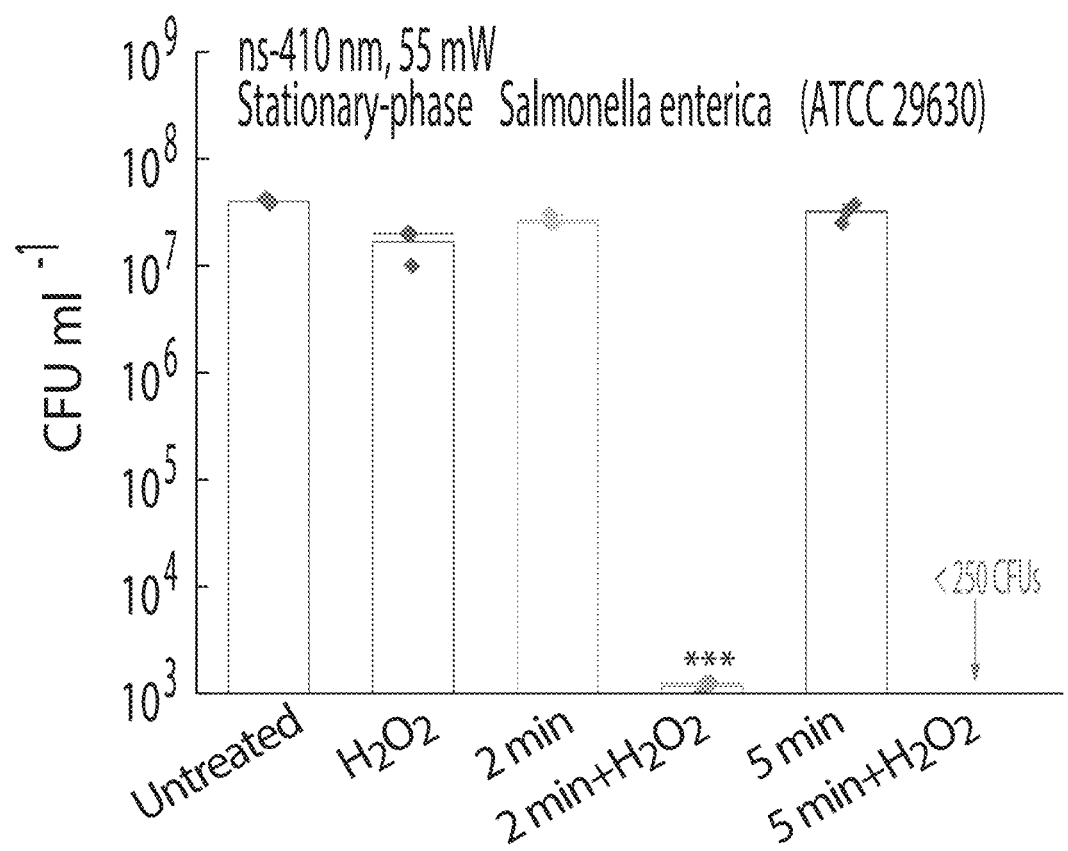

Example 2: Photo-inactivation of Catalase Sensitizes a Wide Range of Bacteria to Low-Concentration $H_2O_2$ Catalase is an essential detoxifying enzyme in bacteria encountering various endogenous or exogenous stress (Nakamura, K. et al. Microbiology and immunology 56, 48-55 (2012)). When the gene encoding the expression of catalase is mutant, pathogens are more susceptible to the environmental stress (Mandell, G. L., J Clin Invest 55, 561-566, doi:10.1172/jci107963 (1975)). Whether exogenous addition of low-concentration $H_2O_2$ could eliminate those 'traumatized' pathogens was investigated. As shown in FIG. 5, photoinactivation of catalase (15 J/cm2) alone didn't reduce the MRSA burden (FIG. 5a), *P. aeruginosa* burden (FIG. 5b), and *Salmonella enterica* burden (FIG. 5c) significantly. Moreover, low-concentration $H_2O_2$ (22 mM) didn't exert any significant antimicrobial effect against both MRSA and *P. aeruginosa* (FIG. 5). However, subsequent administration of low-concentration $H_2O_2$ after photoinactivation of catalase significantly reduced the MRSA and *P. aeruginosa* burden (≥3-log 10 reduction, FIG. 5). Interestingly, the bacterial killing trend versus irradiance wavelength is similar to that of photoinactivation of catalase versus irradiance wavelength. Noteworthy, low-concentration $H_2O_2$ combined with 410 nm exposure (15 J/cm2) achieved total eradication of *P. aeruginosa* (FIG. 5b).

Example 3: Photoinactivation of Catalase and Low-Concentration Hydrogen Peroxide Create a Synergistic Effect There is a synergistic effect between photoinactivation of catalase and low-concentration hydrogen peroxide to eliminate stationary-phase MRSA USA300 and stationary-phase *Pseudomonas aeruginosa*. FIG. 5a depicts the synergistic results in a bar-graph. CFU ml-1 (colony-forming unit) designates the bacterial burden. 'Untreated' refers to the original stationary-phase MRSA without any exogenous treatment. '$H_2O_2$ (22 mM, 0.075%)' and 'ns-light' refer to stationary-phase MRSA with $H_2O_2$ and ns light alone, respectively. As shown in the graph, $H_2O_2$ alone and ns-light alone do not exert any significant killing effect on MRSA, however, ns-410 nm in combination with $H_2O_2$ reduces approximately four orders of magnitude of bacterial burden. The same phenomenon happens with other wavelengths as well. Noteworthy, ns-430 nm or ns-430 nm combined with $H_2O_2$ reduces around 99% of the bacterial burden under the same conditions. ns-450 or ns-460 nm combined with $H_2O_2$ together reduces around 90% of the bacterial burden. ns-470 nm combined with $H_2O_2$ together reduces around 50% of the bacterial burden. ns-480 nm combined with $H_2O_2$ barely exerts an antimicrobial effect. Altogether, the killing effect of $H_2O_2$ is significantly enhanced by blue light photoinactivation of catalase, especially when applied using ns-410 nm. A similar phenomenon occurred with stationary-phase *Pseudomonas aeruginosa*, which is a representative of Gram-negative bacteria (FIG. 5b) and *Salmonella enterica*. By employing ns-410 nm combined with $H_2O_2$ to *Salmonella enterica*, an enhanced killing effect of around five orders of magnitude was observed (FIG. 5c).

Figure 6:
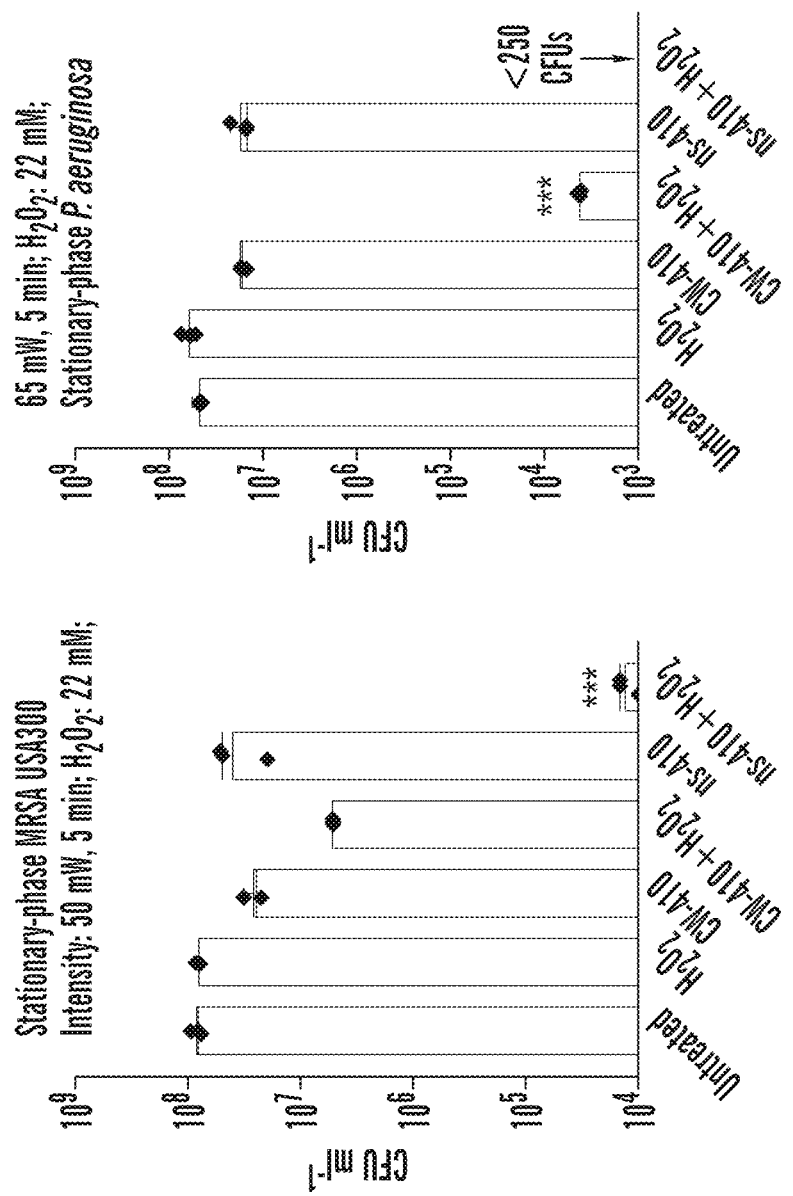
FIG. 6 depicts the killing efficacy comparison between CW-410 nm and ns-410 nm combined with $H_2O_2$ in both stationary-phase MRSA USA300 and *Pseudomonas aeruginosa*. Left and right: CFU ml-1 of stationary-phase MRSA and *P. aeruginosa* under different treatment schemes, respectively. N=3. Data: Mean±SD. ***: significant difference. p<0.001. 250 CFUs: detection of limit.
Figure 8:
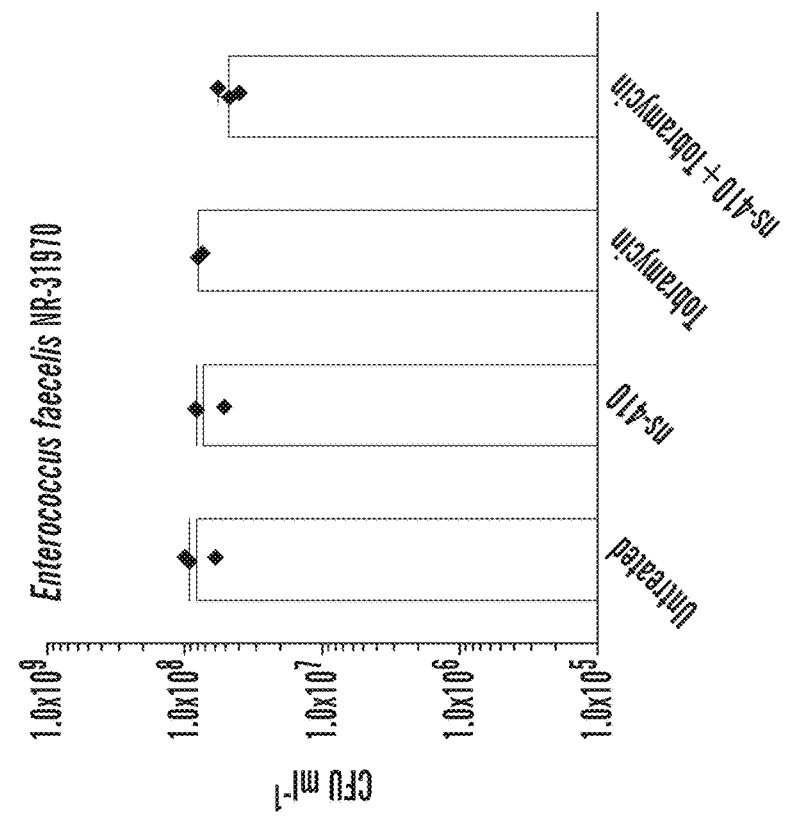
FIG. 8 depicts CFU ml-1 of *Enterococcus faecalis* NR-31970 under different treatment schemes. Tobramycin: 2 μg/ml, 4-hour incubation.

In addition, ns-410 nm combined with $H_2O_2$ is significantly more effective in eliminating microbes compared to CW-410 nm combined with $H_2O_2$ (FIG. 6).

Example 4: Photoinactivation of Catalase Revives Conventional Antibiotics Against a Wide Range of Bacteria Besides $H_2O_2$, whether photoinactivation of catalase could synergize with conventional antibiotics was investigated, especially for antibiotics that can generate the downstream intracellular ROS. Tobramycin, a representative of aminoglycoside, is an example. Tobramycin can induce downstream ROS burst (Dwyer, D. J. et al. Proceedings of the National Academy of Sciences 111, E2100-E2109, doi: 10.1073/pnas.1401876111 (2014)), thus the combination of photoinactivation of catalase and tobramycin administration, together, was tested to see whether an enhanced effect was observed.

Figure 7:
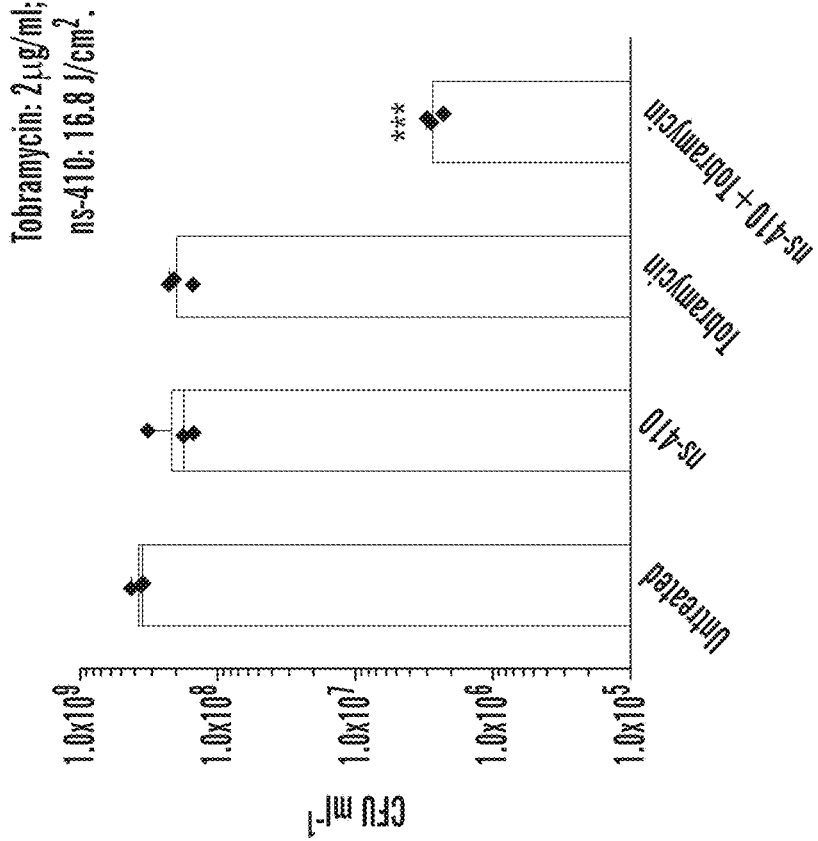
FIG. 7 depicts CFU ml-1 of *E. coli* BW25113 under different treatment schemes. Tobramycin: 2 μg/ml, 4-hour incubation. ***: p<0.001, student unpaired t-test.

Interestingly, enhanced killing effect was observed in the combination-treated group (FIG. 7). More than 100 times enhancement suggests that photoinactivation of catalase indeed accelerates the antimicrobial effect of ROS-generating antibiotics. As a control, the same treatment schemes were tested on a catalase-negative *Enterococcus* strain, *Enterococcus faecalis* NR-31970, which did not produce any enhanced killing effect (FIG. 7). Altogether, this indicates that photoinactivation of catalase helps to revive traditional antibiotics against catalase-positive pathogens.

Figure 9H:
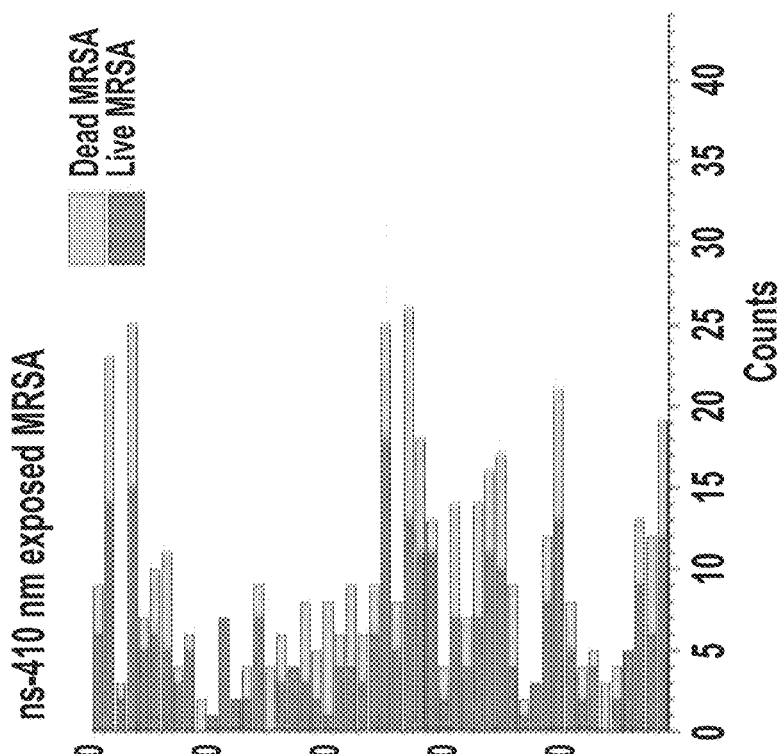
Figure 9G:
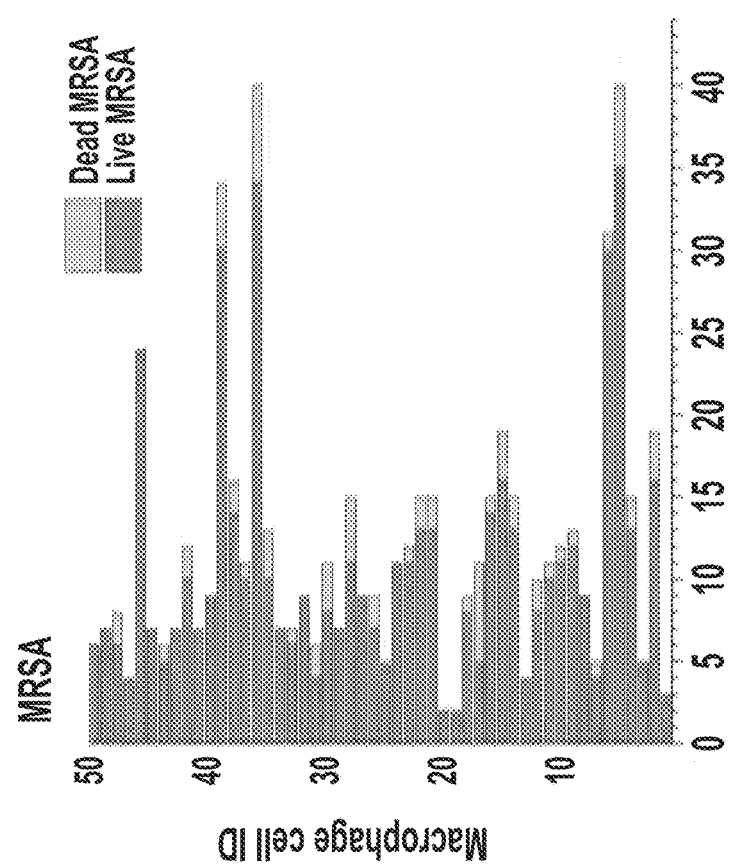

Example 5: Photoinactivation of Catalase Assists Macrophage Cells Against Intracellular Pathogens Neutrophils and macrophage cells are highly essential phagocytic cells that serve as the first line of defense of the innate immune system (Segal, A. W., Annu Rev Immunol 23, 197-223, doi:10.1146/annurev.immunol.23.021704.115653 (2005)). Catalase, which is encoded by gene, katA, confers indispensable resistance to the antimicrobial agents released by immune cells (Flannagan, R., Heit, B. & Heinrichs, D., Pathogens 4, 826-868 (2015)). Based on these facts, it was hypothesized that photoinactivation of catalase could assist immune cells to eliminate extracellular and intracellular pathogens. To test the potential assistance effect, a fluorescent Live/Dead assay was used to visualize the intracellular live/dead bacteria after ns-410 nm exposure. A higher percent of dead MRSA was observed intracellularly (FIG. 9).

In conclusion, photoinactivation of catalase significantly boosts the efficacy of low-concentration $H_2O_2$, ROS-generating antibiotics, and immune cells against broad-spectrum bacteria, including the notorious drug-resistant gram-negative bacteria.

The following materials and methods were employed throughout Examples 5.-9.

Chemicals and fungal strains: DMSO (W387520, Sigma Aldrich), amphotericin B (A9528-100 MG, Sigma Aldrich), ergosterol (AC1178100050, 98%, ACROS Organics). YPD broth (Y1375, Sigma Aldrich). YPD agar (Y1500, Sigma Aldrich). PrestoBlue cell viability assay (A13262, Thermo Fisher Scientific). *Candida albicans* SC5314, the test of fungal strains used see Table 1.

TABLE 1

Fungal strains utilized for amp B imaging experiments.

| Pathogen | Strain | Number |
| --- | --- | --- |
| C. albicans | SC5314 | SC5314 |
| C. glabrata | ATCC2001 | ATCC2001 |
| C. tropicalis | C22 | H3222861 |
| C. parapsilosis | C23 | F825987 |
| C. lusitaniae | C30 | S1591976 |
| Candida auris | Lung | From MGH--commonly used in MKM lab |
| Candida haemulonii | CAU-13 | AR-0393 |
| Candida duobushaemulonii | CAU-14 | AR-0394 |
| Candida haemulonii | CAU-15 | AR-0395 |
| Kodameae ohmeri | CAU-16 | AR-0396 |
| C. albicans | Ca C13 | |
| C. albicans | Ca C14 | |
| C. glabrata | Cg C1 | |
| C. glabrata | Cg C2 | |
| Candida krusei | CAU-17 | AR-0397 |

TABLE 1-continued

Fungal strains utilized for amp B imaging experiments.

| Pathogen | Strain | Number |
| --- | --- | --- |
| C. lusitaniae | CAU-18 | AR-0398 |
| Saccharomyces cerevisiae | CAU-19 | AR-0399 |
| C. albicans | Ca C15 | |
| C. albicans | Ca C16 | |
| C. albicans | Ca C17 | |
| Candida krusei | CAU-17 | AR-0397 |
| C. lusitaniae | CAU-18 | AR-0398 |
| Saccharomyces cerevisiae | CAU-19 | AR-0399 |
| C. albicans | Ca C15 | |
| C. albicans | Ca C16 | |
| C. albicans | Ca C17 | |
| Candida auris | CAU4 | AR-0384 |
| | CAU5 | AR-0385 |
| | CAU5 | AR-0386 |
| | CAU7 | AR-0387 |
| | CAU8 | AR-0388 |
| | CAU9 | AR-0389 |

Quantification of catalase from fungus before and after 410 nm exposure: Quantification of catalase both from the pure catalase solution and fungal solution were achieved by a fluorescent amplex red catalase kit. Basically, 25 µl of analyte were incubated with 25 µl (40 µM of $H_2O_2$) for 30 min at room temperature. Then 50 µl of working solution (100 µM Amplex Red reagent containing 0.4 U/ml horseradish peroxidase) were added to the abovementioned mixture, and the subsequent mixture was incubated for another 30-60 min in the dark. After that, the fluorescence was recorded at an emission of 590 nm when excited at 560 nm.

CFU test to quantify the treatment efficacy: Quantification of antifungal treatment schemes were achieved as following: overnight cultured fungal specimen was washed by sterile PBS. And log-phase fungal pathogens were prepared by dilution into fresh YPD broth at a ratio of 1:50 and cultured for another 2-3 hours at 30° C. with the shaking speed of 200 rpm. After that, the fungal concentration was adjusted to be around 1×108 cells/ml by centrifuging or further dilution with PBS. 10 µl of the above fungal solution was exposed to 410 nm for 5 min (150 mW/cm$^2$). After that, the exposed sample was collected into 990 µl of sterile PBS, then supplemented with treatment agents. Later, CFU of fungal cells was enumerated by serial dilution and cultured in YPD agar plates for 48 hours.

PrestoBlue viability assay: First log-phase fungal pathogens were prepared by diluting overnight-cultured fungal pathogens into fresh YPD broth at a ratio of 1:50 and cultured for another 2-3 hours at 30 C with the shaking speed of 200 rpm. After that, the fungal concentration was adjusted to be around 1×108 cells/ml by centrifuging or further dilution with PBS. 10 µl of the above fungal solution was exposed to 410 nm for 5 min (150 mW/cm$^2$). After that, the exposed sample was collected into 990 µl of sterile PBS, then supplemented with treatment agents. Aliquots were made from the above sample into a 96-well plate, with each well containing 100 µl. Then 100 µl sterile YPD broth and 23 µl of PrestoBlue were added into the same well. Fluorescence signal at 590 nm from each well was recorded in a time-course (up to 18 hours with the interval of 30 min) manner at an excitation of 560 nm. For each strain, in order to know the exact number of fungal pathogens in each well, the corresponding fluorescence signals were recorded from fungal pathogens with known numbers, however no external treatments.

Macrophage-*Candida albicans* interaction unveiled by confocal laser scanning microscopy: As described elsewhere (Yang, X., et al. International journal of nanomedicine 13, 8095 (2018)), murine macrophage cells (RAW 264.7) were cultured in DMEM supplemented with 10% FBS plus penicillin and streptomycin at 37 C with CO2 (5%). Cells were exposed to *Candida albicans* SC5314 (with/without 410 nm exposure) at a multiplicity of infection (MOI) of approximately 10:1 at serum-free DMEM medium. 1 or 2-hours post-infection, RAW 264.7 cells were washed with gentamicin (50 µg/mL, for one hour) to kill extracellular pathogens in DMEM+10% FBS. After that, RAW 264.7 cells were washed with gentamicin (50 µg/mL) and subsequently lysed using 0.1% Triton-X 100 for 3 min. After membrane permeabilization, infected RAW 264.7 cells were stained with Live/Dead stain for 15 min, then samples were fixed in 10% formalin for 10 min. Formalin was washed away prior confocal imaging.

Example 5: 410 nm Exposure Reduces Intracellular Catalase Amount

Figure 10:
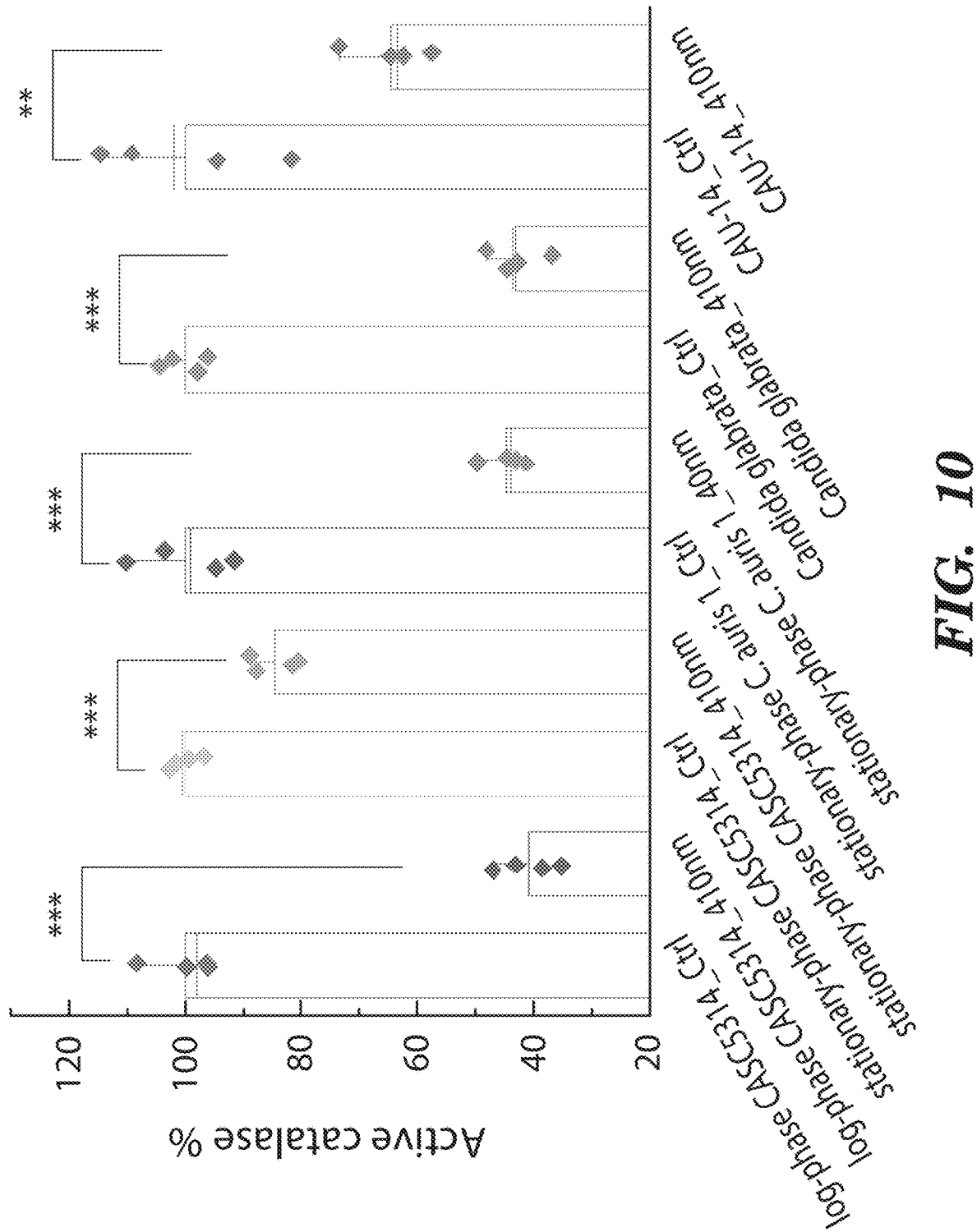
FIG. 10 depicts active catalase percent of various fungal strains with or without 410 nm light exposure. Dose: 410 nm, 150 mW/cm2, 5 min. Fungal concentration: 106 cells/ ml. *C. albicans* CASC5314: wild-type *Candida albicans*.

It is known that most fungal pathogens are catalase positive (Hansberg, W., et al. Arch Biochem Biophys 525, 170-180 (2012)). To test whether 410 nm exposure could cause the loss of catalase activity, the same approach to quantify the intracellular catalase amount by the amplex red catalase kit was utilized before and after 410 nm exposure. Catalase from various fungal pathogens, either log-phase or stationary-phase could be significantly inactivated by 410 nm exposure (FIG. 10). Noteworthy, catalase from notorious *Candida auris* strain reduced by 60% after only 5-min 410 nm exposure.

Figure 11:
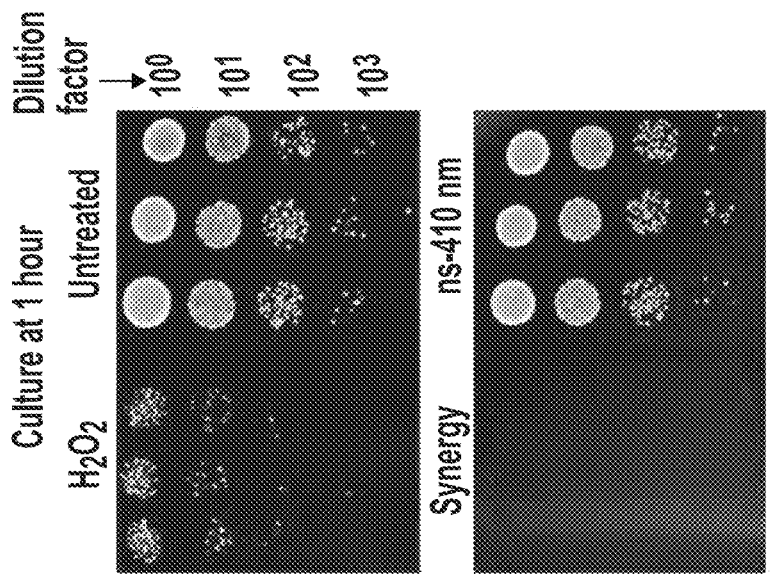
FIG. 11 depicts CFU results of *C. albicans* CASC5314 after different treatment schemes. (Left) Time-killing assay of CASC5314 after various treatment schemes. (Right) Spread plates of CASC5314 after 1-hour incubation at different treatment schemes.
Figure 11:
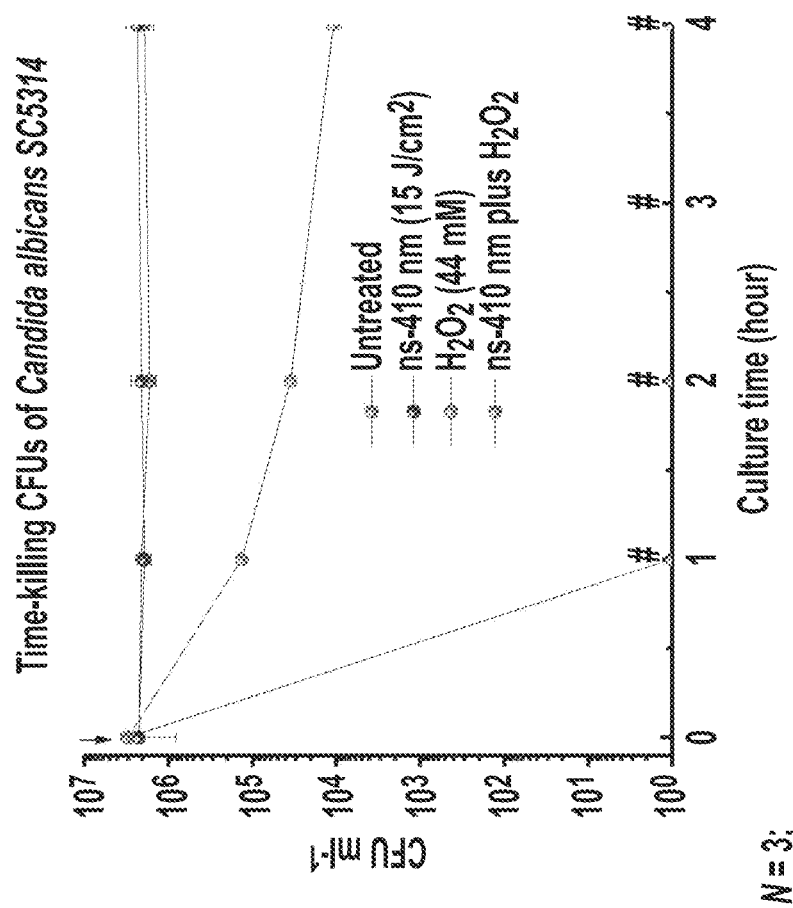

Example 7: Photoinactivation of Catalase in Combination with $H_2O_2$ Achieved Total Eradication of *C. albicans* SC5314 by CFU Assay Since catalase was effectively inactivated among various fungal strains, whether photoinactivation of catalase could sensitize fungal strains to external $H_2O_2$ attack was investigated. With further administration of low-concentration $H_2O_2$ after 410 nm exposure, eradication was achieved after combinational treatments (FIG. 11). Noteworthy, there was more than five orders of magnitude enhancement of the function of $H_2O_2$ after photoinactivation of catalase (FIG. 11).

Figure 12:
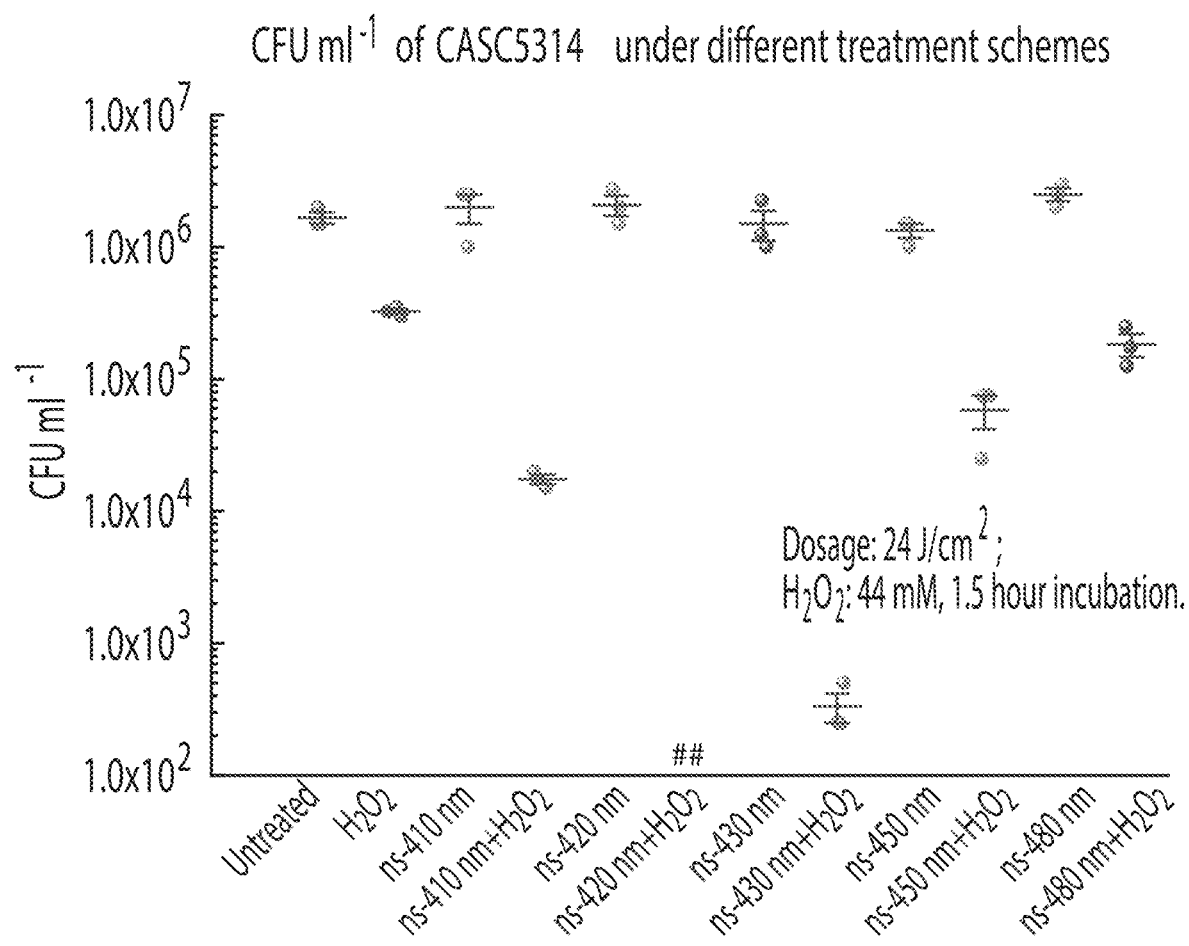
FIG. 12 depicts the synergistic effect between photoinactivation of catalase under various wavelengths and low-concentration hydrogen peroxide to eliminate stationary-phase CASC5314. CFU ml-1 of CASC5314 after treatments under the combination between $H_2O_2$ and various wavelengths. Dosage: 40 mW/cm$^2$, 24 J/cm$^2$. H2O2: 44 mM, 1.5-hour incubation. Data: Mean±SEM (N=3). ##: detection limit.
Figure 13A:
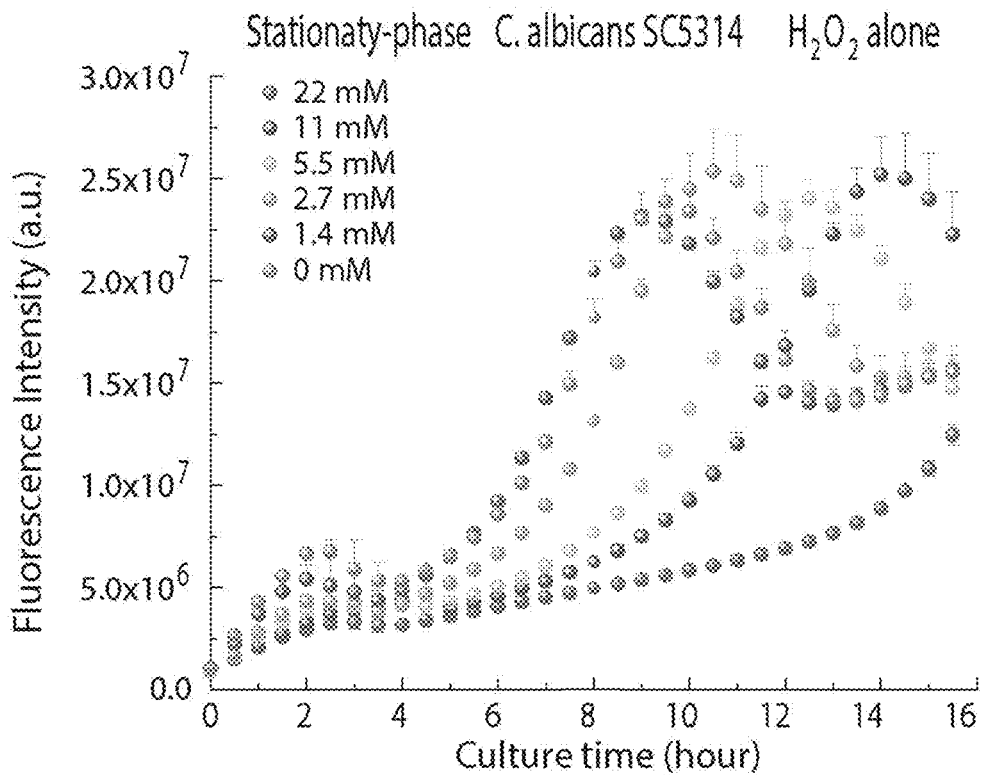
FIGS. 13A-13D depict fluorescence signals of PrestoBlue from CASC5314 under various treatment schemes.
Figure 13B:
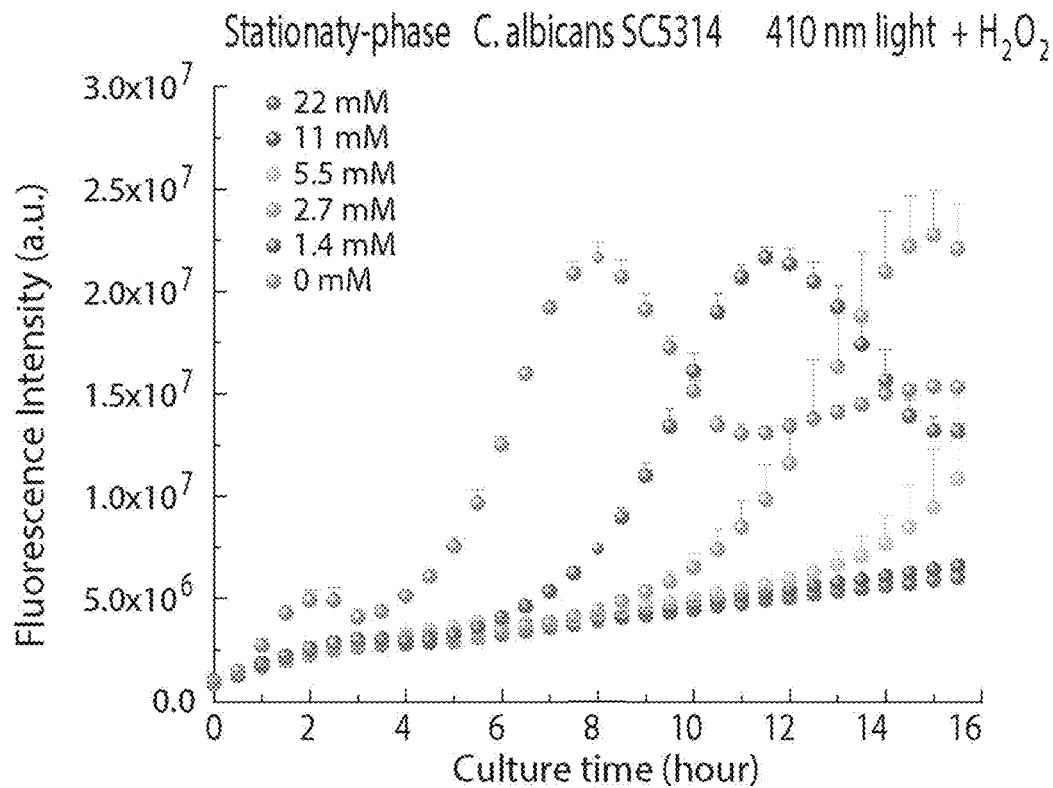
Figure 13C:
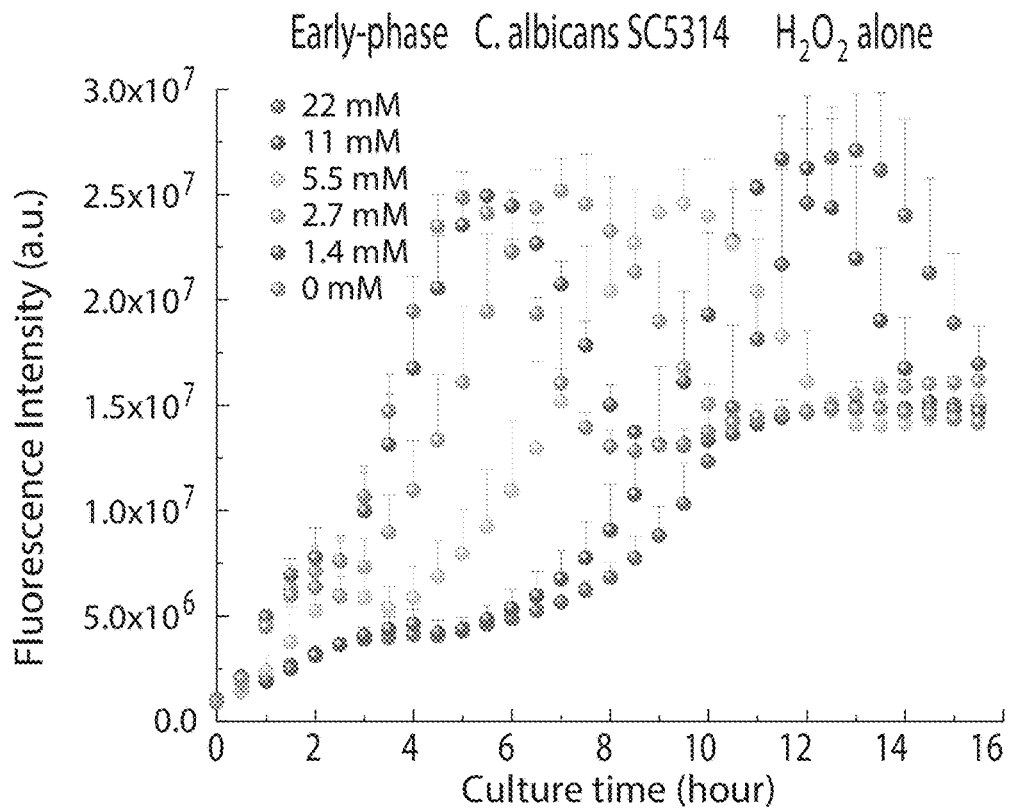
Figure 13D:
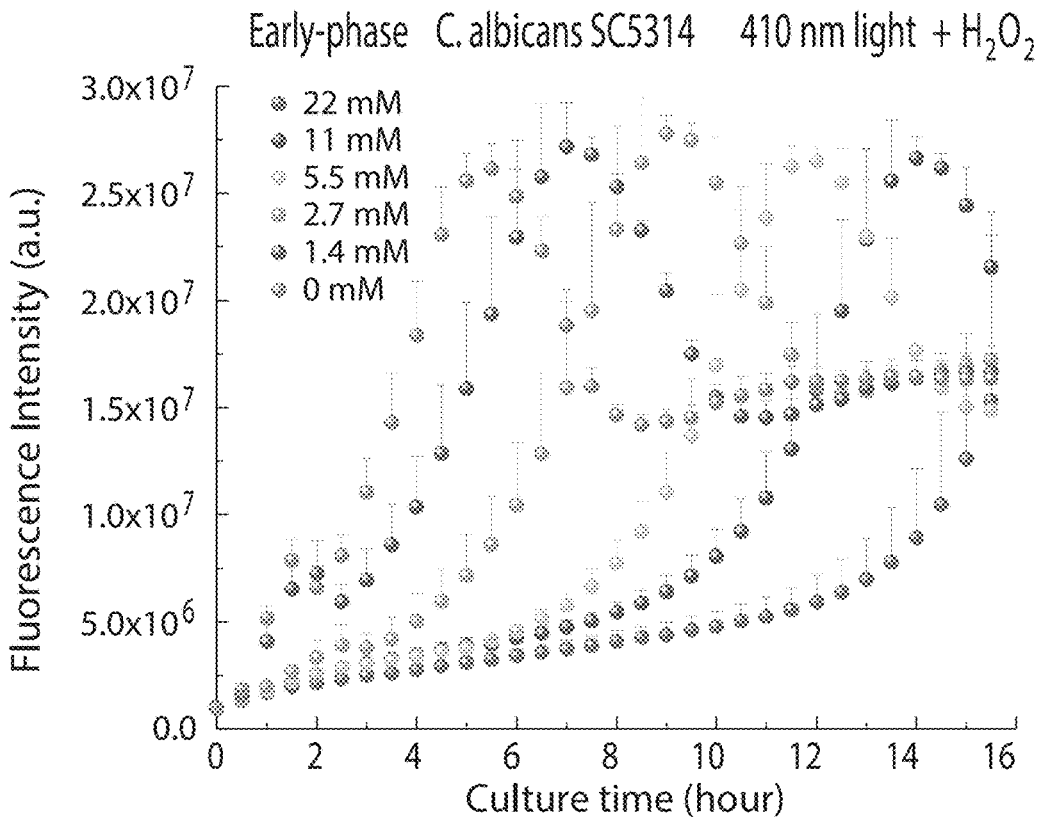

Synergism between photoinactivation of catalase and $H_2O_2$ to eliminate *Candida albicans* SC5314 was also observed. The result is shown by a scatter plot in FIG. 12. CFU ml-1 (colony-forming unit) refers to the number of bacterial burden. 'Untreated' means the original stationary-phase SC5314 without any exogenous treatment. 'H2O2 (44 mM, 0.15%) and 'ns-light' means stationary-phase SC5314 with H2O2 and ns-light alone, respectively. As shown in FIG. 12, $H_2O_2$ alone and ns-light alone doesn't exert significant killing effect on CASC5314, however, ns-light in combination with $H_2O_2$ reduces around four orders of magnitude of bacterial burden. Especially, ns-410 or ns-420, ns-430 combined with $H_2O_2$ achieved total eradication. ns-450 or ns-480 nm combined with $H_2O_2$ reduced a similar amount of fungal burden as $H_2O_2$-alone. Altogether, the killing effect of $H_2O_2$ is significantly enhanced by photoinactivation of catalase by blue light, especially by ns-410-ns-430 nm. Therefore, an effective synergy exists between photoinactivation of catalase under the blue light range and $H_2O_2$ to eliminate CASC5314.

Example 8: Photoinactivation of Catalase in Combination with $H_2O_2$ Achieved Efficient Eradication of Broad-Spectrum Fungal Species by PrestoBlue Assay To further confirm that this combinational therapy works as well for other fungal strains, more clinical fungal strains were tested for feasibility of this synergistic therapy. Unlike bacteria, fungal cells growth is slower, with each colony forming after around 48 hours. Thus, a high-throughput method, PrestoBlue viability assay, was used to measure the treatment efficacy. As shown in FIG. 13, the utilization of PrestoBlue could achieve the same killing effect as the CFU assay. Interestingly, log-phase and stationary-phase CASC5314 demonstrate different behavior towards the combinational killing, presumably because of the difference in metabolic activity between these two states. However, either log-phase or stationary-phase, photoinactivation of catalase always boosts the killing effect of low-concentration $H_2O_2$. This synergistic therapy was tested among more than twenty different clinical fungal isolates, and significant killing was consistently found among them.

Example 9: *Candida auris* Strains Are Sensitive to 410 nm Light Exposure

Apart from $H_2O_2$, whether photoinactivation of catalase was capable of synergizing with conventional antifungal agents, such as azoles or amphotericin B (amp B) was investigated. Similar to some classes of antibiotics, amp B kills fungi partly due to the oxidative damage (Belenky, P. et al. Fungicidal drugs induce a common oxidative-damage cellular death pathway. Cell Rep 3, 350-358, doi:10.1016/j.celrep.2012.12.021 (2013). Therefore, to test our hypothesis, the PrestoBlue assay was conducted after the treatments of photoinactivation of catalase and subsequent addition of amp B against various clinical fungal isolates, including *C. auris* strains.

Figure 14:
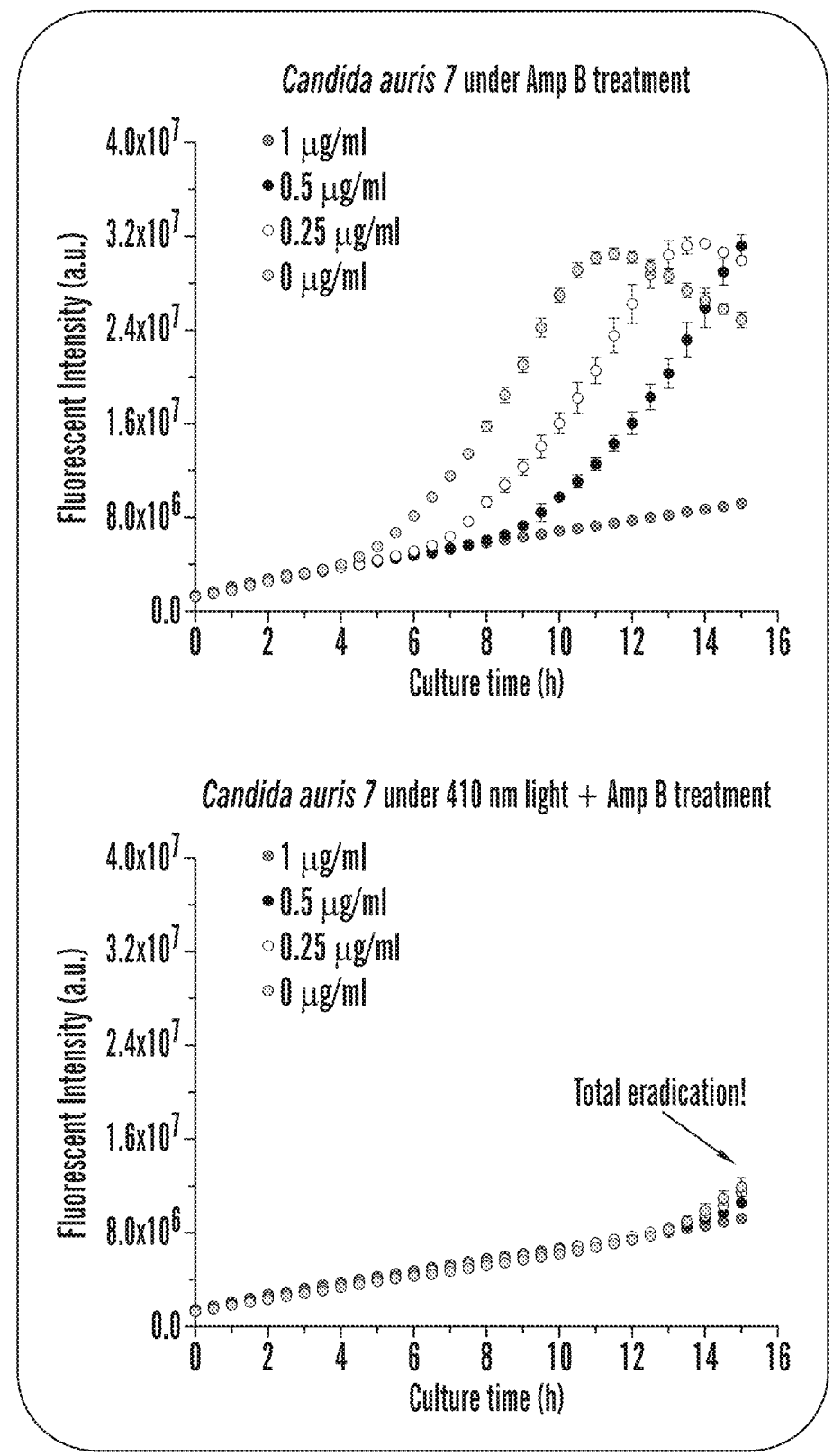
FIG. 14 depicts Fluorescence signals of PrestoBlue of three different *C. auris* strains under different treatment schemes: Amp B alone-treated groups and 410 nm plus amp B-treated groups.
Figure 14:
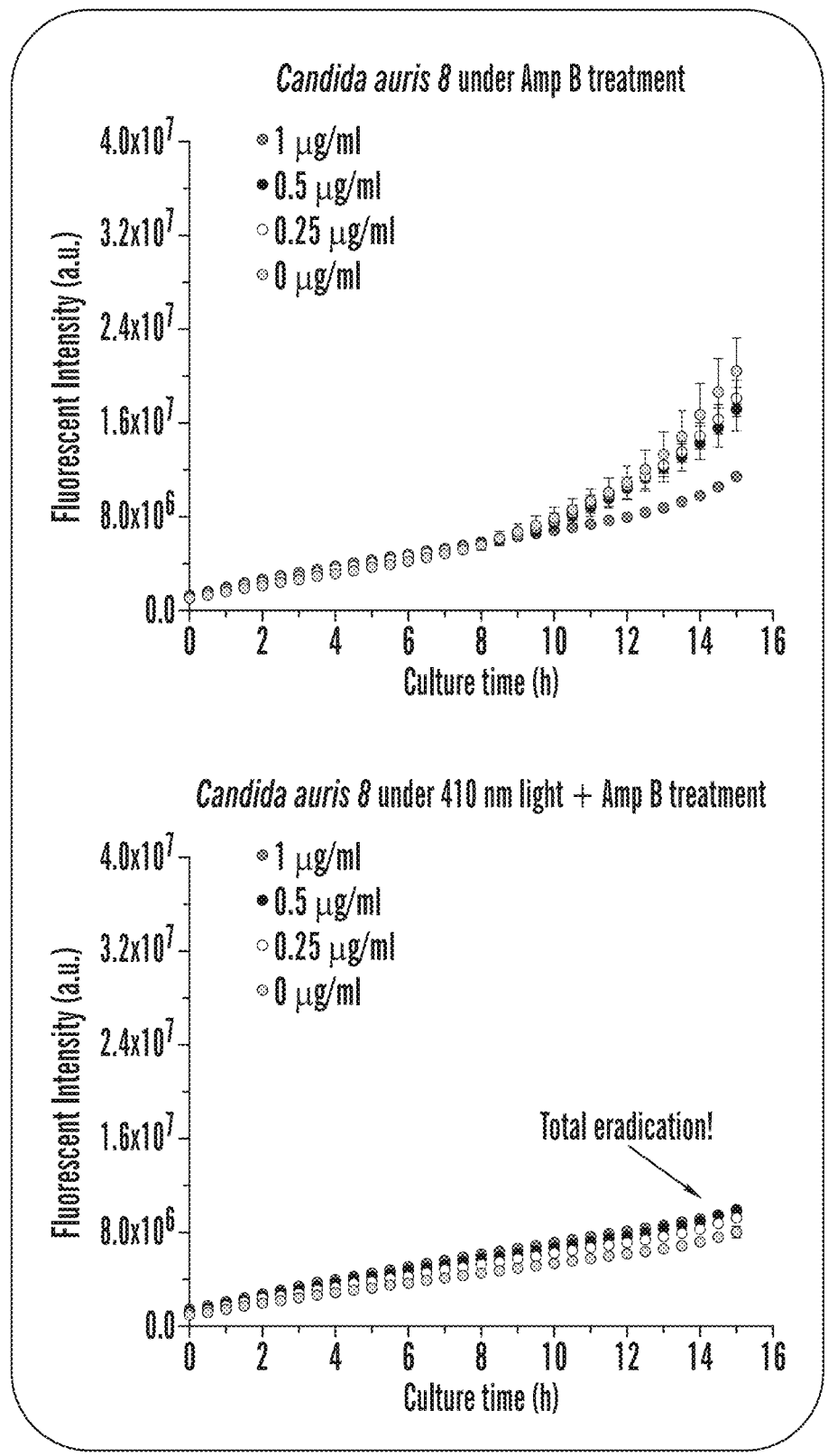
Figure 14:
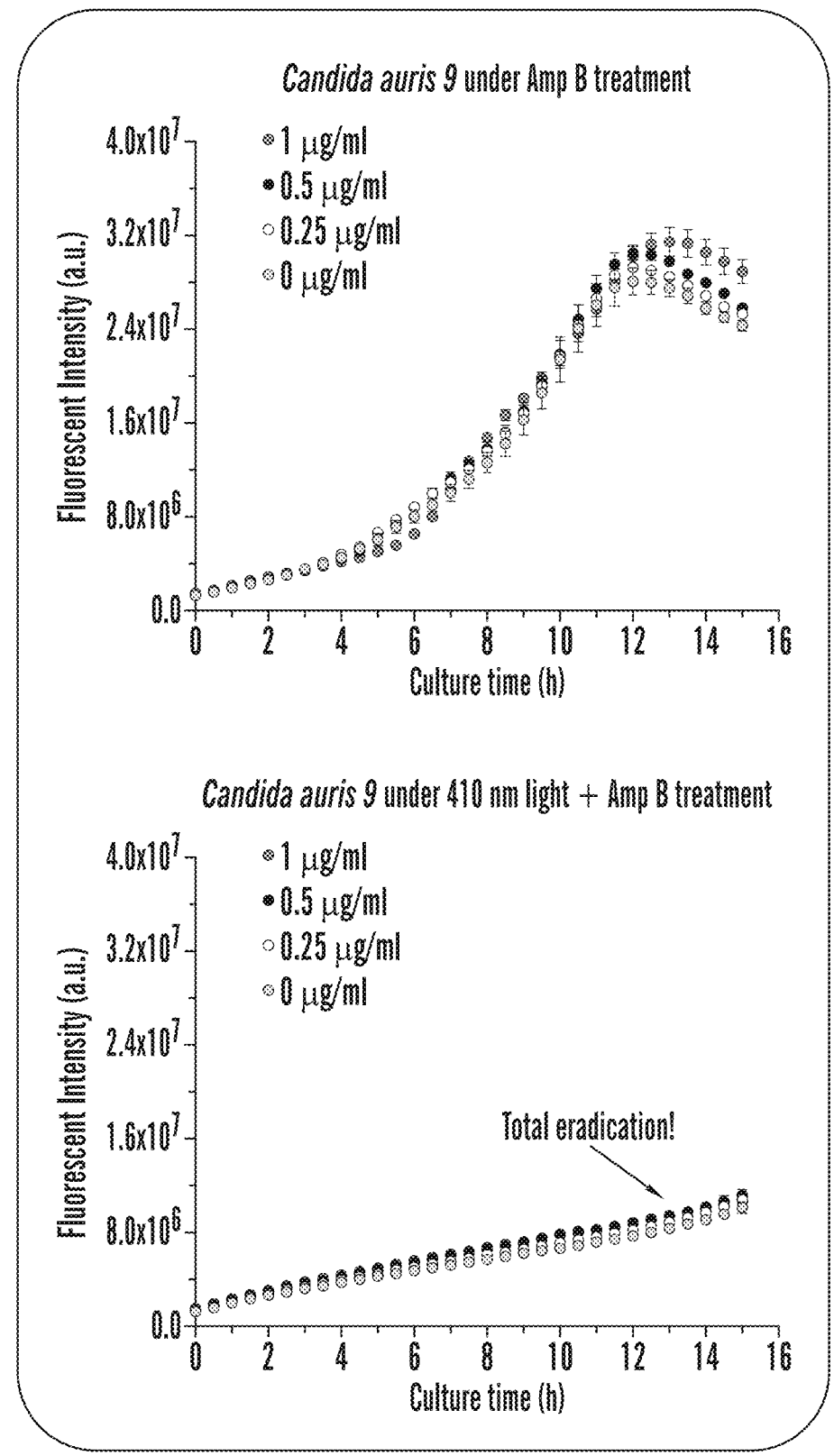

Interestingly, without the assistance of photoinactivation of catalase, some *C. auris* strains were resilient to amp B (FIG. 14). Nonetheless, photoinactivation of catalase achieved total eradication of *C. auris* strains regardless of the addition of amp B. Ten *C. auris* strains were tested and they demonstrated the same behavior. This means *C. auris* strains are exceptionally sensitive to blue light exposure.

Example 10: Photoinactivation of Catalase Inhibits the Formation of Hyphae of *C. albicans*, and Assists Macrophage Cells to Phagocytose Host immune cells play important roles against external evasive pathogens. Catalase holds an essential role during the battle between *C. albicans* and neutrophils or macrophage cells (Pradhan, A. et al. Elevated catalase expression in a fungal pathogen is a double-edged sword of iron. Plos Pathog 13, e1006405 (2017). Thus, whether photoinactivation of catalase could assist macrophage cells against *C. albicans* was examined. To visualize this effect, RAW 264.7 cells were infected with *C. albicans* and 410 nm-exposed *C. albicans* at a MOI of 10 and labeled with live/dead fluorescence stains.

Figure 15:
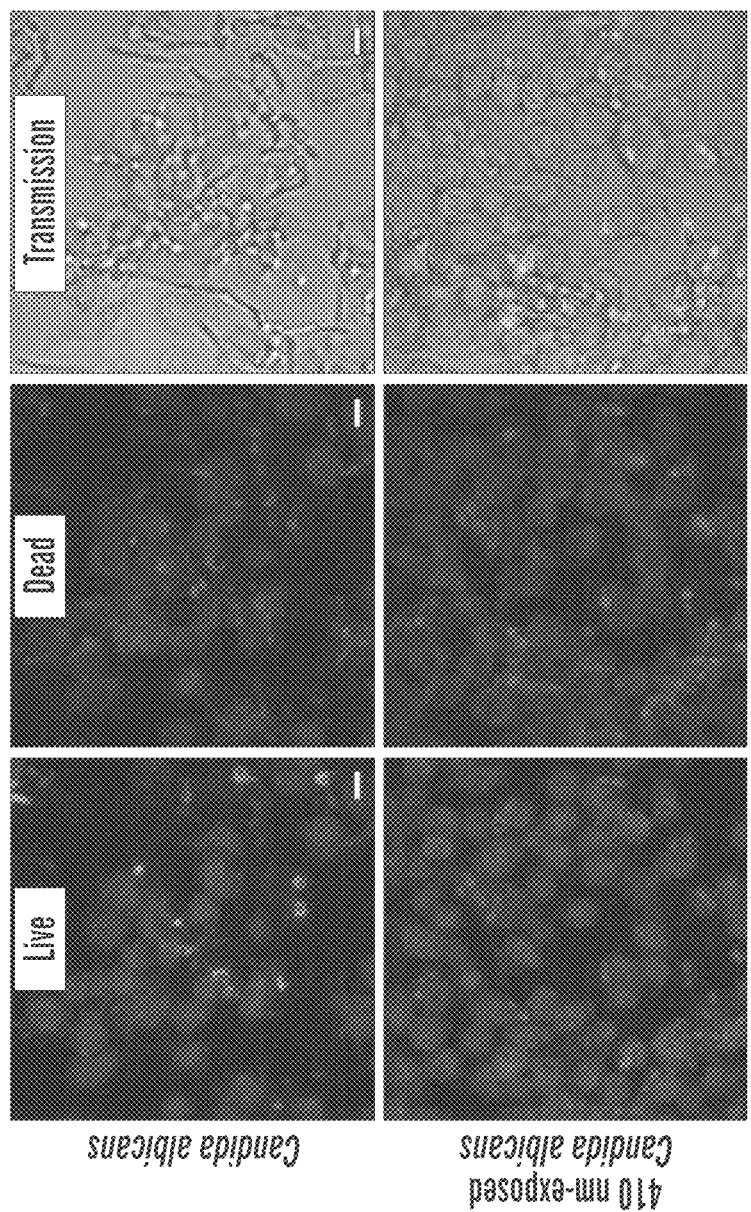
FIG. 15 depicts confocal laser scanning imaging of live/ dead *C. albicans* after infecting RAW264.7 macrophage cells.

As shown in FIG. 15, untreated *C. albicans* stay as hyphae form and pierced through macrophage cells. Whereas 410 nm-exposed *C. albicans* remained as dead 'yeast' form intracellularly.

In summary, photoinactivation of catalase in combination with low-concentration $H_2O_2$ presents an effective and novel approach to eliminate broad-spectrum fungus and fungal infections.

Figure 16:
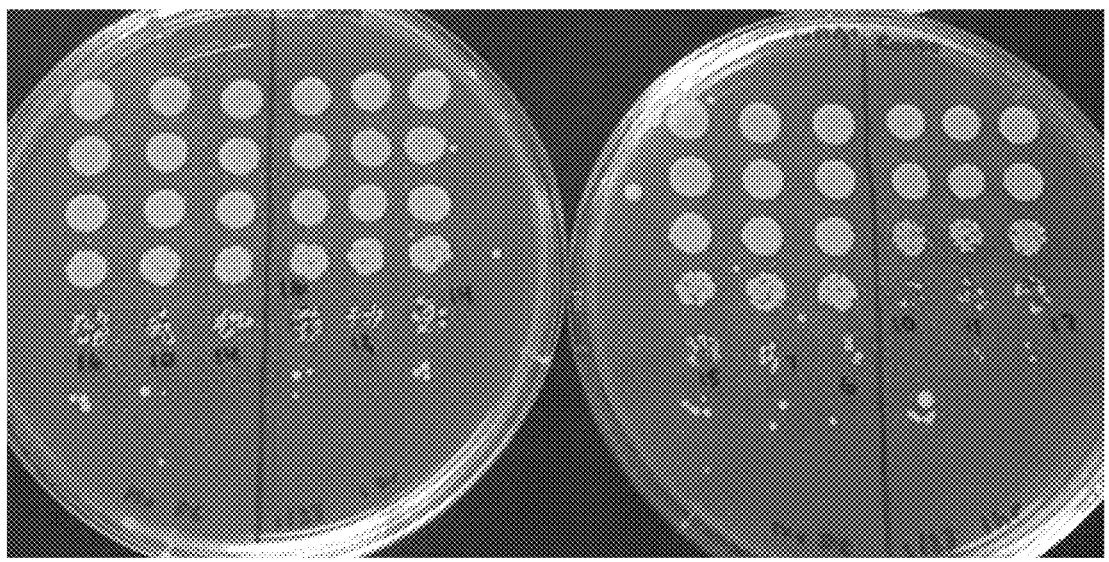
FIG. 16 depicts photoinactivation of catalase in combination with silver cation kills MRSA. Shown in the images are spread agar plates of MRSA USA300 under different treatment schemes.

Example 11: Photoinactivation of Catalase in Combination With ROS Activating Agent Silver Cation Synergistically Kills Microbes Electromagnetic energy having a wavelength of ns-410 nm combined with 10 µM of silver cation eliminated about 90% of MRSA one hour after treatment, whereas ns-410 nm alone or silver cation alone does not exert any significant antimicrobial effect (FIG. 16).

Photoinactivation of catalase and low-concentration silver cation synergistically eliminate E. coli BW25113 as well. The result is shown by scatter plots in FIG. 17. CFU ml-1 (colony-forming unit) is designated as the amount of bacterial burden. 'Untreated' refers to the original E. coli BW25113 without any exogenous treatment. '0.5 µM $Ag^+$' and 'CW-410' or 'ns-light' refers to E. coli BW25113 with 0.5 µM $Ag^+$ and ns-410 alone, respectively. 0.5 µM $Ag^+$ alone and CW-410 alone or ns-410 alone doesn't exert any significant killing effect on E. coli, however, ns-410 in combination with 0.5 µM $Ag^+$ reduces around 99% of bacterial burden (FIG. 17). The same phenomenon happens at other wavelengths as well. Noteworthy, CW-410 combined with 0.5 µM $Ag^+$ didn't significantly reduce bacterial burden under the same conditions. Our results are consistent for both 30 and 60 minutes after treatments.

From the foregoing description, it will be apparent that variations and modifications may be made to the invention described herein to adopt it to various usages and conditions. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

REFERENCES

All patents, patent applications and publications mentioned in this specification are herein incorporated by reference to the same extent as if each independent patent and publication was specifically and individually indicated to be incorporated by reference.

The invention claimed is:

1. A method of treating a catalase-positive microbe in contact with a tissue, said method comprising the steps of: applying visible light to the catalase-positive microbe at a wavelength of about 400 nm to about 430 nm, wherein catalase within the catalase-positive microbe is inactivated, and contacting the microbe with a reactive oxygen species generating agent.

2. The method of claim 1, wherein the wavelength is about 410 nm.

3. The method of claim 1, wherein the dose of the light is about 5 $J/cm^2$ to about 200 $J/cm^2$.

4. The method of claim 1, wherein the dose of light is less than about 200 $J/cm^2$.

5. The method of claim 1, wherein the catalase-positive microbe is a fungal or bacterial microbe and the light is provided by a pulsed nanosecond laser.

6. The method of claim 1, wherein the catalase-positive microbe is a fungal or bacterial microbe and the light is provided by a continuous wave LED.

7. The method of claim 1, wherein the catalase-positive microbe is a fungal or bacterial microbe and the light is provided by a pulsed LED.

8. The method of claim 1, wherein the reactive oxygen species generating agent is hydrogen peroxide.

9. The method of claim 8, wherein the concentration of hydrogen peroxide is 3.0% or less.

10. A method of producing a synergistic antimicrobial effect for a catalase-positive microbe in contact with a tissue, said method comprising the steps of: applying visible light to the catalase-positive microbe at a wavelength of about 400 nm to about 460 nm, wherein catalase within the catalase-positive microbe is inactivated, and contacting the microbe with a reactive oxygen species generating agent, thereby producing the synergistic antimicrobial effect.

11. A method of treating a subject infected with a catalase-positive microbe, said method comprising the steps of: applying visible light to the catalase-positive microbe at a wavelength of about 400 nm to about 430 nm, wherein catalase within the catalase- positive microbe is inactivated, and contacting the microbe with a reactive oxygen species generating agent.

12. The method of claim 11, wherein the wavelength is about 410 nm.

13. The method of claim 11, wherein the dose of the light is about 5 $J/cm^2$ to about 200 $J/cm^2$.

14. The method of claim 11, wherein the dose of light is less than 200 $J/cm^2$.

15. The method of claim 11, wherein the catalase-positive microbe is a fungal or bacterial microbe and the light is provided by a pulsed nanosecond laser.

16. The method of claim 11, wherein the catalase-positive microbe is a fungal or bacterial microbe and the light is provided by a continuous wave LED.

17. The method of claim 11, wherein the catalase-positive microbe is a fungal or bacterial microbe and the light is provided by a pulsed LED.

18. The method of claim 11, wherein the reactive oxygen species generating agent is hydrogen peroxide.

19. The method of claim 18, wherein the hydrogen peroxide is 3.0% or less.

20. The method of claim 1, wherein the catalase-positive microbe is killed.

21. The method of claim 11, wherein the catalase-positive microbe is killed.

* * * * *

UNITED STATES PATENT AND TRADEMARK OFFICE
CERTIFICATE OF CORRECTION

| | |
|---|---|
| PATENT NO. | : 12,064,641 B2 |
| APPLICATION NO. | : 18/303778 |
| DATED | : August 20, 2024 |
| INVENTOR(S) | : Dong et al. |

It is certified that error appears in the above-identified patent and that said Letters Patent is hereby corrected as shown below:

On the Title Page

Item (56) References Cited, OTHER PUBLICATIONS, Page 4, Column 2, Line 48: Please correct "Ciao" to read --Liao--

Signed and Sealed this
Twenty-sixth Day of November, 2024

Katherine Kelly Vidal
*Director of the United States Patent and Trademark Office*